US007801685B2

(12) United States Patent
Ho

(10) Patent No.: US 7,801,685 B2
(45) Date of Patent: Sep. 21, 2010

(54) SYSTEM AND METHOD FOR IMPROVED COMPUTER DRUG DESIGN

(75) Inventor: Chris Meichung Wang Ho, St. Louis, MO (US)

(73) Assignee: Drug Design Methodologies, LLC, St. Louis, MO (US)

( * ) Notice: Subject to any disclaimer, the term of this patent is extended or adjusted under 35 U.S.C. 154(b) by 151 days.

(21) Appl. No.: 11/208,189

(22) Filed: Aug. 19, 2005

(65) Prior Publication Data

US 2006/0041414 A1 Feb. 23, 2006

Related U.S. Application Data

(60) Provisional application No. 60/602,955, filed on Aug. 19, 2004.

(51) Int. Cl.
*G01N 33/48* (2006.01)
*G06G 7/48* (2006.01)

(52) U.S. Cl. .......................................... 702/19; 703/11
(58) Field of Classification Search ....................... None
See application file for complete search history.

(56) References Cited

U.S. PATENT DOCUMENTS

| | | | |
|---|---|---|---|
| 5,434,796 A | 7/1995 | Weininger | |
| 6,219,622 B1 | 4/2001 | Schmidt | |

OTHER PUBLICATIONS

Payne et al., "Iterative minimization techniques for ab initio total-energy calculations: molecular dynamics and conjugate gradients," Reviews of Modern Physics, vol. 64, pp. 1045-1097.*

Nicklaus et al., "Conformational Changes of Small Molecules Binding to Proteins", Bioorganic & Medicinal Chemistry, vol. 3 (1995) pp. 441-428.*
Brooks et al., "CHARMM: A Program of Macromolecular Energy, Minimization, and Dynamics Calculations," Journal of Computational Chemistry., vol. 4 (1983) pp. 187-217.*
Head et al., "Validate: A New Method for the Receptor-Based Prediction of Binding Affinities of Novel Ligands", American Chemical Society, vol. 118, No. 16, pp. 3959-3969 (1996).
Lewell et al., "RECAP—Retrosynthetic Combinatorial Analysis Procedure: A Powerful New Technique for Identifying Privileged Molecular Fragments with Useful Applications in Combinatorial Chemistry", American Chemical Society, vol. 38, No. 3, pp. 511-522 (1998).
Weiss, Mark D., "Numerous Tools and Strategies Available for Structure-based Drug Design", pp. 1-6.
Accelrys Ludi Release 4b http://www.msg.ucsf.edu/local/programs/insightII/doc/life/cerius46/Iud/ludiTOC.html, pp. 1-63 (Printed Oct. 4, 2002).
http://www.tripos.com, LeapFrog®, 2005, p. 1-2, USA.
Hevener et al., "Validation of Molecular Docking Programs for Virtual Screening against Dihydropteroate Synthase," Journal of Chemical Information and Modeling, vol. 49, No. 2, pp. 444-460, (2009).
Marrone et al., Structure-Based Drug Design: Computational Advances, Annual Review, Pharmacology and Toxicology, vol. 37, pp. 71-90 (1997).
Reddy et al., Calculation of Relative Differences in the Binding Free Eneries of HIV1 Protease Inhibitors: A Thermodynamic Cycle Perturbation Approach, J. Med. Chem., vol. 37, pp. 1145-1152 (1994).

* cited by examiner

*Primary Examiner*—Marjorie Moran
*Assistant Examiner*—Anna Skibinsky
(74) *Attorney, Agent, or Firm*—Woodard, Emhardt, Moriarty, McNett & Henry LLP

(57) ABSTRACT

A system and method for computer-aided drug design employs adaptive sampling and iterative fitting of multi-atomic subunits. The iterative fitting is performed by successive perturbation of the location of the multi-atomic subunits in directions that reduces potential energy.

6 Claims, 18 Drawing Sheets

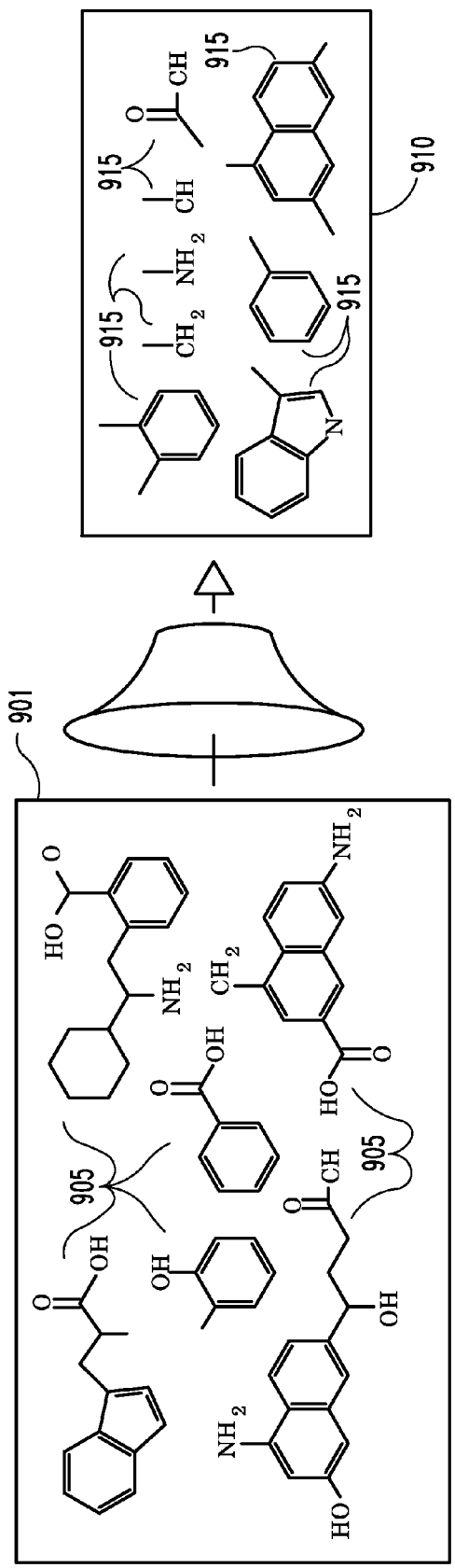
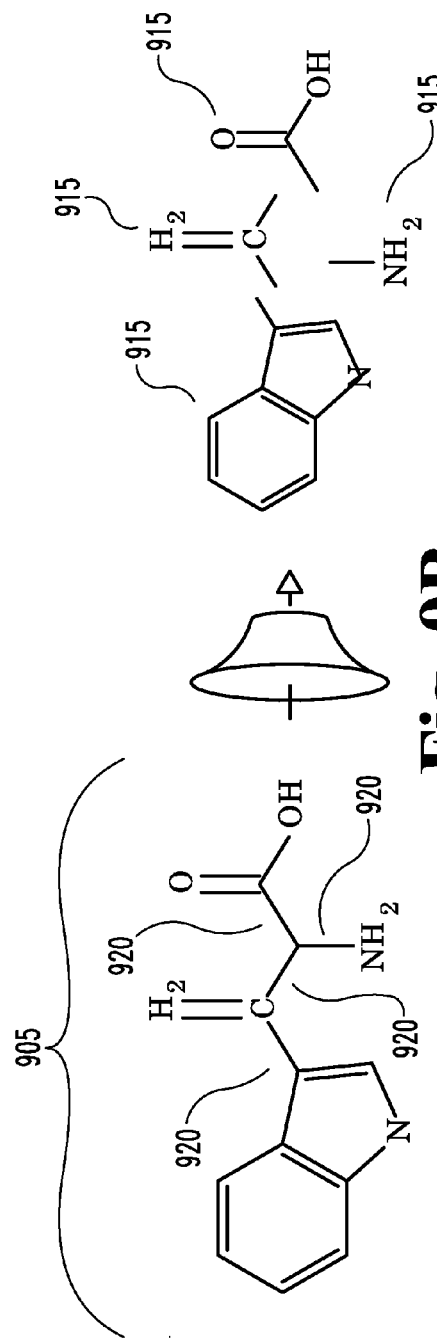
Fig. 9A
Fig. 9B

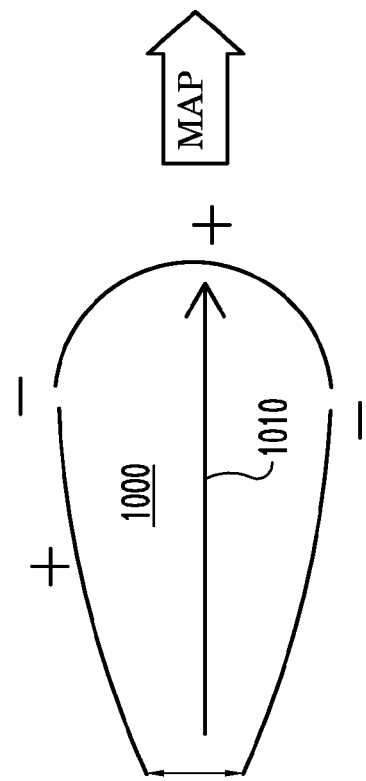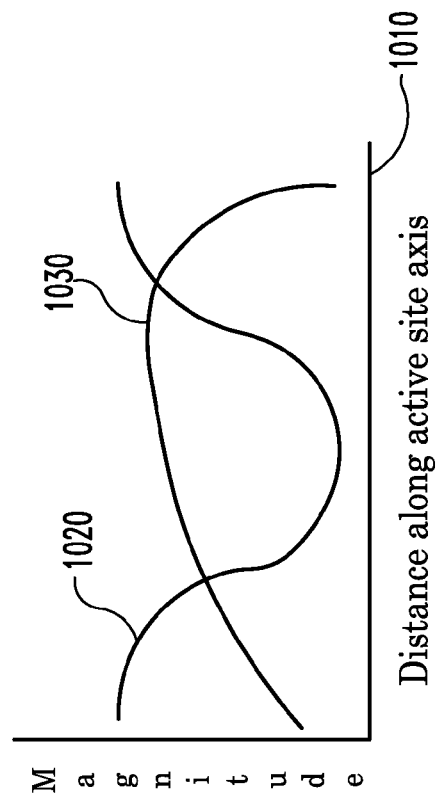
Fig. 10

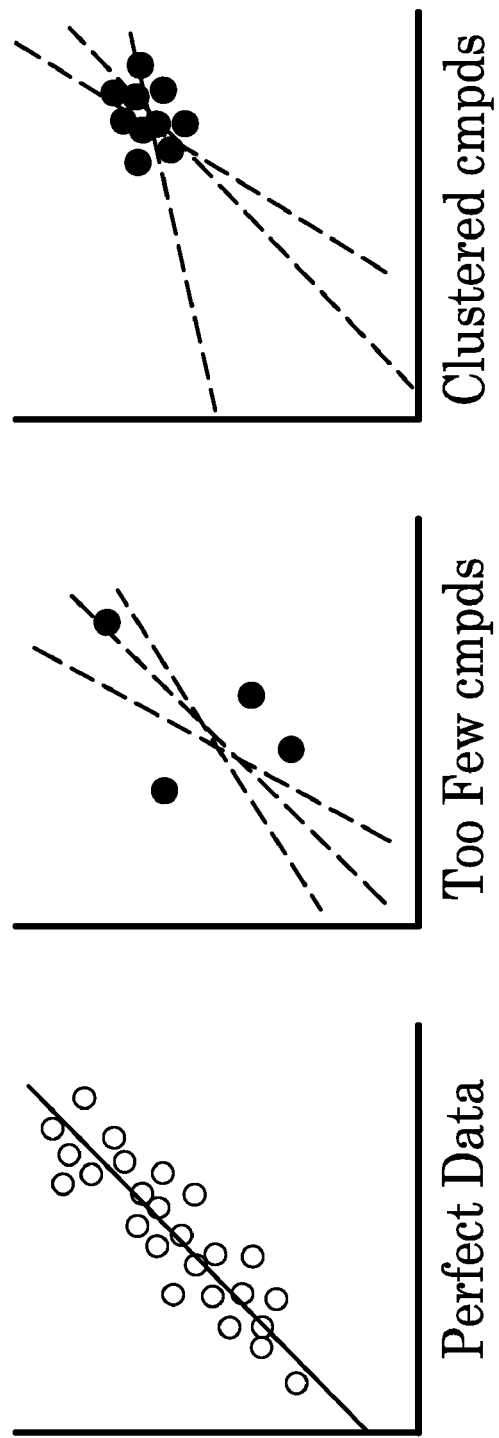

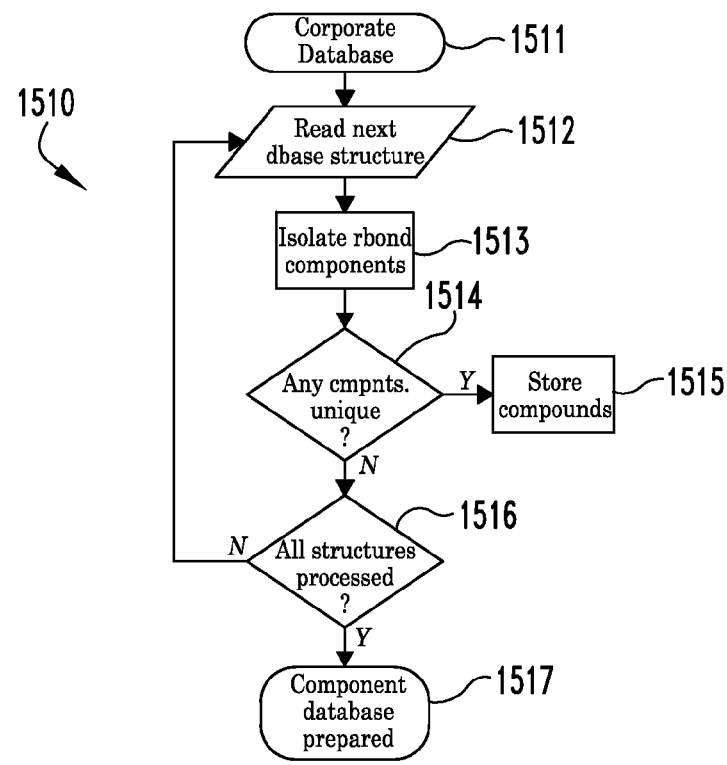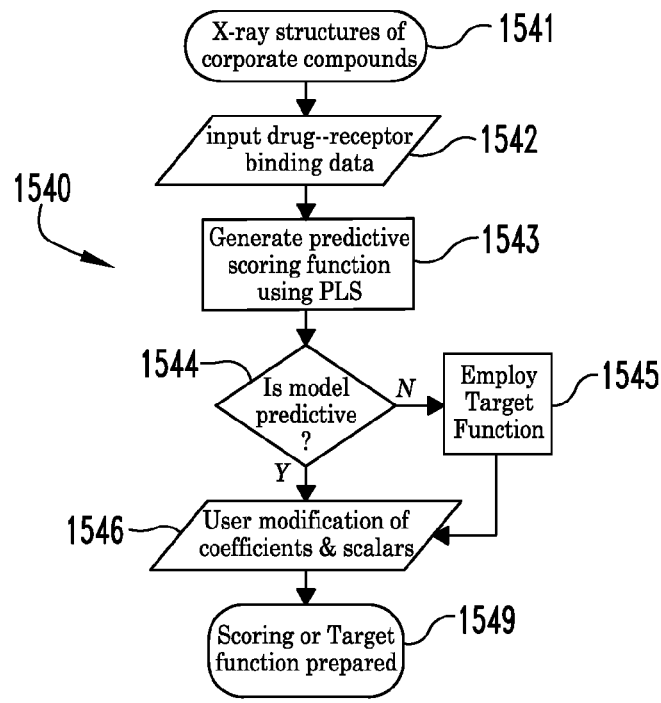
Fig. 15A

SYSTEM AND METHOD FOR IMPROVED COMPUTER DRUG DESIGN

PRIORITY

This utility patent application claims priority from U.S. Provisional Patent Application No. 60/602,955, filed Aug. 19, 2004, and from U.S. Utility patent application Ser. No. 10/288,851, the entire specifications of which are hereby incorporated herein.

BACKGROUND OF THE INVENTION

Discovery and development of drugs is a lengthy, expensive, and often unsuccessful process. Typically, it takes 12 to 16 years, and more than $500 million from the original concept to the market introduction of a new drug. Numerous software packages have been developed to assist in the development of new drugs. Unfortunately, all of these programs must make tradeoffs between completeness of their searching functions and the speed of their computations. In other words, drug design software that includes more efficient computational methods has a better chance of identifying new, useful drugs.

As is known by those skilled in the art, the vast majority of drugs are small molecules designed to bind, interact, and modulate the activity of specific biological receptors. Receptors are proteins that bind and interact with other molecules to perform the numerous functions required for the maintenance of life. They include an immense array of cell-surface receptors (hormone receptors, cell-signaling receptors, neurotransmitter receptors, etc.), enzymes, and other functional proteins. Due to genetic abnormalities, physiologic stresses, or some combination thereof, the number, structure, or function of specific receptors and enzymes may become altered to the point that our well-being is diminished. These alterations may manifest as minor physical symptoms, as in the case of a runny nose due to allergies, or as life threatening and debilitating events, such as sepsis or depression. The role of drugs is to modulate the number, structure, or activity of these receptors to remedy the resulting medical condition.

Enzymes are a subset of receptor-like proteins that are directly responsible for catalyzing the biochemical reactions that sustain life. For example, digestive enzymes act to break down the nutrients of our diet. DNA polymerase and related enzymes are crucial for cell division and replication. Enzymes are genetically programmed to be absolutely specific for their appropriate molecular targets. Any errors could have grave consequences. For example it would likely be fatal if blood-clotting enzymes began activating throughout the body, or if our immune system began attacking our own tissues. Enzymes ensure the specificity of their targets by forming a molecular environment that excludes interactions with inappropriate molecules. The analogy most often mentioned is that of a lock and key. The enzyme is a molecular lock, which contains a keyhole that exhibits a very specific and consistent size and shape. This molecular keyhole is termed the active site of the enzyme and allows interaction with only the appropriate molecular targets. Just as a typical lock is much bigger than the keyhole, the receptor is usually much larger than the active site. The receptor, as specified by our DNA, is a folded protein whose major purpose is to form and maintain the size and shape of the active site. This is illustrated in FIG. 1 using the structure of the HIV-1 protease, indicated generally at 100. The active site is indicated at 110.

The most important aspect of drug design relates to the mechanism by which the active site of a receptor selectively restricts the binding of inappropriate structures. Any potential molecule that can bind to a receptor is called a "ligand." In order for a ligand to bind, it must contain a specific combination of atoms that presents the correct size, shape, and charge composition in order to bind and interact with the receptor. The ligand must possess the molecular "key" that binds the receptor lock.

FIG. 2 schematically shows a typical ligand-receptor binding interaction. The ligand is indicated at 200, and the walls of the active site 110 are shown at 210. For ligand-receptor interaction to occur, the ligand 200 must be complementary in size and shape to the receptor active site 110. This is known as "steric complementarity." The more close the fit between the ligand and receptor, the tighter the interaction becomes. If a molecule varies from a functioning ligand by even a single atom in the wrong place, it may not fit properly, and therefore not interact with the receptor, or not interact strongly enough. Note that, although the schematic illustration of FIG. 2 is two-dimensional, both ligand 200 and active site 110 are three-dimensional.

In addition to steric complementarity, electrostatic interactions influence ligand binding. Charged receptor atoms often surround the active site 110, imparting a localized charge in specific regions of the active site. In FIG. 2, regions of relative negative charge are indicated at 220, while regions of relative positive charge are shown at 230. It will be appreciated by those skilled in the art that opposite charges attract while similar charges repel. Electrostatic complementarity further restricts the binding of inappropriate molecules, since the ligand 200 must contain correctly placed complementary charged atoms for it to interact with the active site 110.

It will be appreciated by those skilled in the art that the strongest driving force for ligand and receptor binding is "hydrophobic interaction." Nearly two-thirds of the body is water, and this aqueous milieu surrounds all our cells. In order for ligand and receptor to interact, there must be a driving force that compels the ligand to leave the water and bind to the receptor. The hydrophobicity of a ligand is what causes this. Hydrophobicity is a measure of how "greasy" a compound is. It can be roughly approximated by the percentage of hydrogen and carbon in the molecule. This force can be demonstrated by placing a few drops of oil in a cup of water. The oil is composed of hydrocarbon chains and is highly hydrophobic. The oil droplets will rapidly coalesce into a single globule in order to avoid the water, which is highly polar. As shown in FIG. 2, the active site may contain a mixture of hydrophobic pockets and regions that are more polar. Since the hydrophobic portions of the ligand and receptor prefer to be juxtaposed, the arrangement of hydrophobic surfaces provides yet another way that receptors can limit the binding of inappropriate targets.

As discussed above, there are numerous potential interactions between ligand and receptor. Depending upon the size of the active site, there may be a myriad steric, electrostatic, and hydrophobic contacts. However, some are more important than others. The specific interactions that are crucial for ligand recognition and binding by the receptor are called the "pharmacophore." Usually, these are the interactions that directly factor into the structural integrity of a receptor or are involved in the mechanism of its action. Only a molecule that presents the pharmacophore to the receptor properly interacts with the active site. This is crucial to the design of pharmaceuticals since any successful drug must incorporate the appropriate chemical structures and present the pharmacophore to the receptor.

This is illustrated in FIG. 3. A first molecule 310 is a native ligand bound within the active site. Assume that through biochemical investigation, we determine that the phenyl ring 322 and the carboxylic acid group 324 are vital to receptor interaction. Thus, we deduce that these two groups must be the pharmacophore 320 that a ligand must present to the receptor for binding. In future drugs that we develop to mimic the native ligand 310, we must include these two pharmacophoric elements for successful binding to occur. For example, the first derivative compound 330 in which a bicyclic group has been substituted maintains the pharmacophore and retains its complementary size and shape. The derivative compound 330 therefore has a reasonable chance of successfully binding. However, any drug that we develop which lacks a complete pharmacophore, such as the second derivative compound 340 shown in FIG. 3, may not interact with the receptor target.

When a medical condition exists where a drug could be beneficial, extensive scientific study must first be done in order to determine the biological and biochemical problems that underlie the disease process. This often takes years of study in order to characterize the targets for a potential drug. The reason is that nearly all biological processes in the human body are tightly interconnected. Altering the behavior of select receptors or enzymes may have detrimental effects with other systems. These are the side effects that occur with nearly all drugs. Furthermore, the human body is a homeostatic machine, and always attempts to achieve equilibrium. As a result, the body will attempt to counteract any pharmacotherapeutic intervention.

Once a receptor target has been established and well characterized, the process of ligand design begins. The designed ligand must complement the active site of the receptor target. Steric, electrostatic, and hydrophobic complementarity must be established, as discussed above. The pharmacophore must be presented to the receptor in order for recognition and binding to occur. Otherwise, the designed ligand will have no chance of interacting with the receptor.

In addition to adequately binding the receptor, the biochemical mechanism of the receptor target must be taken into consideration. FIGS. 4A and 4B schematically represent the biochemical mechanism of a protease 400. A protease is an enzyme that cleaves proteins and peptides. FIG. 4A shows that a protease 400 recognizes a specific group of atoms 410, that is a peptide bond in a ligand 450. If the peptide bond 410 is present at a specific position in the active site when the ligand 450 binds, it is cleaved by the protease with the addition of water ($H_2O$) to form two separate fragments 420. If the goal is to inactivate this protease, any designed ligand must not possess this peptide bond at the same position. Otherwise, it will simply be cleaved by the protease 400, and the protease 400 will continue to function unperturbed. However, the ligand 450 can be modified to produce a different ligand 455, in which the peptide bond 410 is no longer present as shown in FIG. 4B. If the ligand 455 is bound by the enzyme 400, the enzyme 400 will not be able to cleave it. The enzyme 400 would therefore be inactivated, as the ligand 455 remains lodged in the active site 110.

Once the active site region 110 and the mechanism of action of the target receptor have been characterized, a suitable ligand must be designed. This is typically the most demanding task of the entire drug design process. The optimal combination of atoms and functional groups to complement the receptor is often the natural ligand of the receptor. This is usually an unacceptable candidate for a drug. This may be, for example, because the natural ligand is inactivated by the receptor, as described above, or because it is not feasible to commercially manufacture the natural ligand. Therefore, alternative combinations of chemical structures must be devised.

Those skilled in the art will appreciate that the design of novel ligands is often restricted by what chemists are physically able to synthesize. It is of no use to design the ultimate drug if it cannot be manufactured. Each atom type has a specific size, charge, and geometry with respect to the number and types of neighboring atoms that it can be joined to. The entire field of chemistry is predicated on the establishment of synthetic rules for the construction and manipulation of various combinations of atoms and functional groups. These chemical rules govern the design and synthesis of postulated ligand candidates. Within these rules, the drug developer must creatively propose suitable chemical structures that satisfy the requirements discussed above.

Finally, there are biological considerations to the development of new drugs. For example, the liver is the major organ of detoxification in the human body. Any drug that is taken undergoes a number of chemical reactions in the liver as the body attempts to neutralize foreign substances. This set of reactions is well characterized, and a great deal of knowledge exists as to how drugs are modified as the body eliminates them. For another, even more important example, various chemical structures are highly toxic to biological systems, and these are also well characterized. These constraints must also be taken under consideration as novel drugs are developed.

As discussed above, the development of any potential drug begins with scientific study to determine the biochemistry behind a medical problem for which pharmaceutical intervention is possible. This allows the determination of specific receptor targets that must be modulated to alter their activity in some way. Once these targets have been identified, compounds must be found that will interact with the receptors in some fashion. At this initial stage of drug development, it does not matter what effect the compounds have on the targets. The goal is simply to find anything that binds to the receptor in any fashion.

A typical drug-discovery pipeline is outlined in FIG. 5, shown generally at 500. The first step 520 is to use biological data 510 to determine an "assay" for the receptor. An assay is a chemical or biological test that turns positive when a suitable binding agent interacts with the receptor. Usually, this test is some form of colorimetric assay, in which an indicator turns a specific color when complementary ligands are present. This assay is then used in mass screening 530, which is a technique whereby hundreds of thousands of compounds can be tested in a matter of days to weeks. Typically, a pharmaceutical company will first screen their entire corporate database of known compounds. The reason is that if a successful match is found, the database compound is usually very well characterized. Furthermore, synthetic methods will be known for this compound. This enables the company to rapidly prototype a candidate ligand whose chemistry is well known.

If a successful match is found, the initial hit is called a "lead compound" 540. The lead compound 540 is usually a weakly binding ligand with minimal receptor activity. The binding of this structure to the receptor is then studied at 550 to determine the interactions that foster the ligand-receptor association. If the receptor is water soluble, there is a chance that x-ray crystallographic analysis can be employed to determine the three-dimensional structure of the ligand bound to the receptor at the atomic level. This is a very powerful tool because it allows scientists to directly visualize a snapshot of the individual atoms of the ligand as they reside within the receptor. This snapshot is referred to as the "crystal structure" of the ligand-receptor complex. Unfortunately, not all complexes can be analyzed in this manner. However, if a crystal structure can be determined, a strategy can then be developed based upon this characterization to improve and optimize the binding of the lead compound. From this point onward, a cycle of iterative chemical refinement and testing continues at 560 until a clinically active compound 570 is found. The techniques most often used to refine drugs at 560 are combinatorial chemistry and structure-based design. The clinically active compound 570 is then tested with patients in clinical trials at 580.

Combinatorial chemistry is one technique that aids in the refinement of the lead compound 540. Combinatorial chemistry is a synthetic tool that can rapidly generate many thousands of lead compound 540 derivatives for testing. A scaffold is employed that contains a portion of the ligand 540 that remains constant. Sites on the scaffold are then designated for derivatization, that is, designated for the addition of substituent functional groups from carefully designed chemical libraries, in a combinatorial fashion. As a result, a multitude of derivative structures, each with different substituent groups, may be rapidly generated in an automated fashion. For example, if a scaffold contains three derivatization sites and the library contains ten groups per site, theoretically 1000 different combinations are possible. By carefully selecting libraries based upon the study of the active site, the derivatization process can be targeted towards optimizing ligand-receptor interaction.

Structure based design (also called rational drug design), on the other hand, is much more focused than combinatorial chemistry. Biochemical laws of ligand-receptor association discussed above are used to postulate ligand refinements to improve binding. For example, as discussed above, steric complementarity is vital to tight receptor binding. Using the crystal structure of the complex, regions of the ligand that fit poorly within the active site can be identified, and chemical changes to improve complementarity with the receptor can be postulated. In a similar fashion, functional groups on the ligand can be changed in order to augment electrostatic complementarity with the receptor. However, the danger in altering any portion of the ligand is the effect on the remaining ligand structures. Modifying even a single atom in the middle of the ligand can drastically change the shape of the overall structure. Even though complementarity in one portion of the ligand might be improved by the chemical revision, the overall binding might be severely compromised. This is an important shortcoming of rational design procedures.

Computer aided drug design generally follows one of two strategies: de novo design and drug optimization. De novo design refers to construction of virtual lead compounds entirely through computer simulation. For the most part, de novo design has been unsuccessful. In order to make the calculations that simulate ligand construction and receptor-binding affinity run in a finite period of time, assumptions significant approximations, and numerous algorithmic shortcuts are generally required. This greatly diminishes the accuracy of any calculated ligand-receptor interaction. Thus, de novo design can postulate numerous chemical structures that can potentially complement the active site; however, the calculated binding affinity has little or no correlation with reality. Furthermore, de novo design often generates undesired structures, such as toxic or chemically unstable structures. Therefore, a large fraction of the potential ligands identified by de novo design are useless as a commercial drug.

Computer aided drug optimization, however, is an important tool in drug research. Drug optimization begins with a lead compound 540, which may have been identified by mass screening, through combinatorial chemistry, by x-ray crystallography, or some other means. Small modifications are then made to generate derivative compounds using structure-based design to improve binding affinity. Because the changes are relatively small the validity of the computed binding affinities of the derivatives is relatively high. The best of the derivatives can be tested to verify the accuracy of the calculated binding affinities. The process continues iteratively until satisfactory binding ligands are produced.

Prior art computer-aided drug design packages generally fall into one of three main genres: scanners, builders, and hybrids.

All database search programs fall into the scanner category. Scanner type programs are typically used for lead compound screening. FIG. 6A illustrates how these programs are used. A lead compound 540 whose binding structure has been determined resides within an active site. From biochemical analysis of the ligand-receptor interaction, the pharmacophore is determined. For example, in the lead compound 540 shown in FIG. 6A, it might be determined that three ligand groups make up the pharmacophore 620: a phenyl ring 612, an amide hydrogen 614, and a hydroxyl group 616. The pharmacophore 620 is transformed into a query 630 that specifies the three-dimensional relationship between the functional groups of the pharmacophore 620.

FIG. 6B illustrates the process by which a scanner package identifies potential new drugs. The scanner package requires a database 650 of compounds whose three-dimensional structures are known. The query 630 is then used to search the database 650 for compounds that mimic the pharmacophore 620 and can potentially bind to the receptor target. The scanner package then outputs a set of candidates 660.

Scanners have a number of advantages. In database search programs the user has complete control over the query specifications. This allows for the retrieval of structures that meet the requirements of the pharmacophore 620 and have a better opportunity to complement the receptor. Furthermore, because these programs use a database 650 of known compounds, synthetic feasibility is assured. These programs are typically highly optimized for speed, which allows for the rapid determination of potential binding ligands. Furthermore, since compounds are retrieved that mirror the query, no scoring functions that estimate receptor-binding affinity are required.

However, the scanner relies on the assumption that the three-dimensional structure stored in the database is representative of biological reality. Although this can be true of small molecules, larger structures are often too flexible for the assumption to hold true. Thus, scanners may miss important potential lead compounds that can flex to form a structure with a high binding affinity. Furthermore, scanners cannot generate new lead compounds—they are completely dependent upon the database 650 of structures with which it is supplied. Therefore, scanners cannot identify new structures, and their potential solutions are biased by the database they employ. Furthermore, generating a large database may require a great deal of manpower and funding, imposing a burden to commercial companies and potentially rendering scanner type software useless to academic institutions.

Builder-type programs may be used for de novo ligand design if a substantial portion of the ligand is modified. However, they are best used for the optimization of lead compounds. Like scanners, builder programs use a database of structures. However, a builder's database contains fragments and chemical building blocks instead of complete compounds. In order to optimize a lead compound with a builder, areas of the compound that poorly complement the corresponding receptor region must be identified, as shown in FIG. 7. The lead compound 710 contains a stable, tight-binding region 712, and a phenyl ring 714 that should be replaced to improve receptor complementarity. Builder-type programs require the attachment point of the weak-binding portion as input, shown at 716 on the example lead compound 710. The software then removes the offending ligand region and uses the attachment point 716 to create a population of derivatives by adding, deleting, and substituting fragments 718 chosen from the builder's component database to fill the active site. The binding energies of the resulting derivative ligands are then calculated. Those structures that augment binding are retained while those that do not are discarded. This process repeats as the new population of structures is then processed to generate the next round of derivatives. By making incremental changes iteratively, these programs generate a set of ligands with improved receptor complementarity over time.

Builder programs require less investment to use than scanners because the database is easier to generate. Furthermore, the component database is often built into the software itself. The combinatorial addition of fragments offers a vast number of potential derivative structures. Because components from numerous chemical classes are typically included, builder programs can automatically generate a diverse set of chemical solutions, which contributes to the creation of novel ligands. In addition, builders can also be used to optimize the hits that result from mass screening.

Unfortunately, the combinatorial attachment of such diverse chemical components also leads to the generation of synthetically unfeasible and chemically unstable structures. Also, although a diverse set of chemical building blocks is used, the manner in which they are attached is typically up to the developer of the software. Decisions such as when a particular component is selected and where it is attached greatly affect the generated structures. These choices reflect the bias of the program developers. Furthermore, the ability of builder programs to generate improved ligands is limited by the inability to accurately calculate the receptor-binding structure and binding affinity, as discussed above.

As with scanner packages, builder-type programs are also limited by their ability to deal with ligand flexibility. Builders attempt to deal with this limitation with "conformational searching." It will be appreciated that a molecule is actually composed of rigid chemical groups separated by rotatable bonds, as defined by the laws of chemistry. These rotatable bonds give a ligand inherent flexibility, so that it can adopt numerous configurations as it attempts to bind within the active site. A snapshot structure of the ligand at any instant in time is called a "conformation," and is defined by the set of torsion angles between rigid groups. The task of conformational searching is to determine the most complementary binding structure from all the permutations of potential shapes the ligand can assume. Because of the combinatorial nature of the problem, searching all the rotatable bond configurations a ligand can adopt is extremely demanding in terms of computer resources. Even with yearly exponential increases in processor speed, the complexity of this problem remains one of the most arduous tasks in computational chemistry.

For example, builders typically employ the "odometer" algorithm to find the best-binding shape of a ligand has several rotatable bonds that can each potentially spin 360 degrees. The odometer algorithm is a systematic sampling of all possible torsion angle combinations. Like an odometer, the first bond is fully rotated 360 degrees before the second bond is incremented. When the second bond is incremented, the first bond is reset and then fully scanned again. This continues until the second bond is fully rotated, at which time the third bond is incremented. Searching continues in this manner until all rotatable bond combinations are eventually sampled. During the conformational search, acceptable torsion angle ranges must be determined for each rotatable bond. When a rotatable bond is incremented, the atoms attached to the "swing arm" are checked against all receptor atoms and ligand groups within the vicinity. If contact exists, then that particular conformer is eliminated, so that only valid ligand conformations that conform to the active site are generated.

The combinatorial nature of this problem leads to an exponential rise in the number of conformations that must be calculated. A ligand with four rotatable bonds that is sampled at ten-degree increments requires evaluation of 1,679,616 different conformations. A ligand with five rotatable bonds sampled at ten-degree increments requires evaluation of over 60 million conformations. A search at 10 degree increments is relatively coarse, and may well overlook crucial ligand conformers that optimally interact with the receptor, especially if the active site is convoluted or forces the ligand to adopt a particular conformation when bound. Ideally, sampling at sub-1-degree increments would ensure a more thorough search. In addition, allowing receptor side-chain flexibility and backbone motion would enable the determination of optimal ligand binding modes.

Since drugs typically contain 10-15 rotatable bonds, conformational searching can easily overwhelm even the fastest computers, despite the development of algorithms that reduce the computational burden of conformational searching by orders of magnitude. Consequently, some builder packages do not implement conformational flexibility at all, or use other short-cuts that severely limit their ability to determine adequate ligand binding conformations. Others use rudimentary, pre-calculated torsion angle scans that lack the resolution to tightly dock compounds within the active site.

Hybrid programs are typically employed in de novo ligand generation. FIG. 8 illustrates the operation of a typical hybrid program. A given active site 810 has three distinct regions 812, 814, and 816. The goal of the hybrid program is to generate a complete ligand that complements the active site 810. To do so, the program employs a combination of scanner and builder algorithms. The program first utilizes a scanner strategy to find components that will complement individual subsites within the active site 810 volume, such as the sets of components 822, 824, and 826 shown in FIG. 8. Individual components are then docked into their respective regions within the active site, as, for example, shown in FIG. 8 with the components 832, 834, and 836. Splicing fragments are then used to join the individual components 832, 834, and 836 into one or more complete ligands 850. Because numerous possible fragments may exist that complement the various active site regions a potentially large number of ligands may be generated by combinatorially linking the various components.

The strength of hybrid programs is in their ability to generate a large number of diverse potential hits. However, they suffer the same shortcomings as all de novo design packages described above: their performance is restricted by the inability to accurately calculate ligand-receptor binding affinity; the combinatorial nature of the algorithm often leads to the generation of chemical structures that violate the laws of physics, are unstable, or are synthetically difficult; and the developer of the software may bias the generation of compounds.

As discussed above, molecular mechanics equations quantitatively determine the potential energy of a ligand-receptor system as a function of its atomic coordinates. Using both derivative and non-derivative approaches, minimization algorithms can be applied to these equations to identify system geometries that correspond to minimum points on the energy surface. The potential energy of a chemical system can be thought of as a multi-dimensional surface, where each dimension represents a quantified measurable parameter—atomic coordinates, bond lengths, torsion angles, and so on. Any grid point on this surface represents the potential energy of a specific set of ligand-receptor atom coordinates. Minimization can be used to mathematically determine the lowest local point "downhill" on the energy surface from the original coordinates. This point should correspond to the coordinates of the nearest local minimum.

The use of minimization to improve sampling efficiency can be understood by reference to a simple, four-atom system shown in FIG. 16A, which has a single rotatable bond. Torsion angles of 0° and 360° give the highest potential energy, since the terminal carbons are aligned. Conversely, when the torsion angle is 180°, the internal energy is minimal, as the terminal carbons are maximally separated. The energy profile for this single rotatable bond is thus a "U"-shaped well, with the energy minimally situated at its lowest point, as shown in FIG. 16B.

Without minimization, a conformational search must employ very small angle increments to ensure that the bottom of the well is thoroughly explored. The multiple arrows in FIG. 16B illustrate this. However, if minimization is employed, a much coarser search can be used, since the minimum energy conformer can be readily determined from any structure that falls within the well. As such, the combinatorial impact of the conformer search can be lessened while improving its accuracy. The importance of this is amplified when considering the myriad poses a ligand can potentially adopt within the active site.

Use of minimization involves some unique complexities. For any system with N atoms, the energy is a function of 3N Cartesian coordinates. Even the most basic force fields contain terms describing bond-stretching, angle-bending, torsion, non-bonded, and Coulomb potential energies. Calculating derivatives for all the energy terms and locating minima numerically is CPU intensive in its own right. In addition, minimizing the receptor adds typically ten-fold more atoms to manage. As such, even the fastest of commercially available minimizers currently requires several minutes to relax a typical ligand-receptor structure. This nullifies any computational advantage gained from employing a rough conformational search. For most real-time applications, including docking, automated ligand refinement, and virtual screening, this timeframe is impractical.

Thus, an improved system and method for computer-aided drug design is needed, in which rapid minimization is used to improve adaptive sampling.

SUMMARY OF THE INVENTION

In a first embodiment of a system for computer-aided drug design, the system includes adaptive sampling functionality and rapid minimization functionality. The rapid minimization functionality employs iterative fitting of multi-atomic subunits by perturbing the location of the multi-atomic subunits in a real-space direction that reduces potential energy.

In a second embodiment of a system for computer-aided drug design, the system includes iterative conformational searching having minimization functionality as an element of conformational searching iterations.

In a third embodiment, a method for designing drugs comprises the following steps: Dividing a ligand into subunits. For each subunit, determining force vectors by identifying steric sources of potential energy for each component atom of a subunit. Scaling the force vectors using molecular mechanics parameters to calculate a real-space direction that will minimize potential energy for the subunit. Determining the optimal six-dimensional coordinates for units using RMS fitting.

BRIEF DESCRIPTION OF THE DRAWINGS

FIGS. 9A and 9B schematically illustrate how a system according to the present invention constructs a component database from a user's structure database.

FIG. 10 schematically illustrates the mapping of chemical characteristics of a receptor for a heuristic active site mapping algorithm suitable for use with a system and method according to the present invention.

FIGS. 14A, 14B, and 14C are graphs showing common problems with the creation of accurate scoring functions.

FIGS. 15A, 15B, and 15C are flowcharts of software for computer-aided drug design according to the present invention.

FIG. 16A is a schematic diagram of a four-atom system having a single rotatable bond. FIG. 16B is a graph of potential energy as a function of the torsion angle in the rotatable bond shown in FIG. 16A.

FIG. 18A illustrates a first iteration processing. FIG. 18B illustrates internal force vectors resulting from external force vectors.

DETAILED DESCRIPTION OF THE PREFERRED EMBODIMENTS

Figure 1:
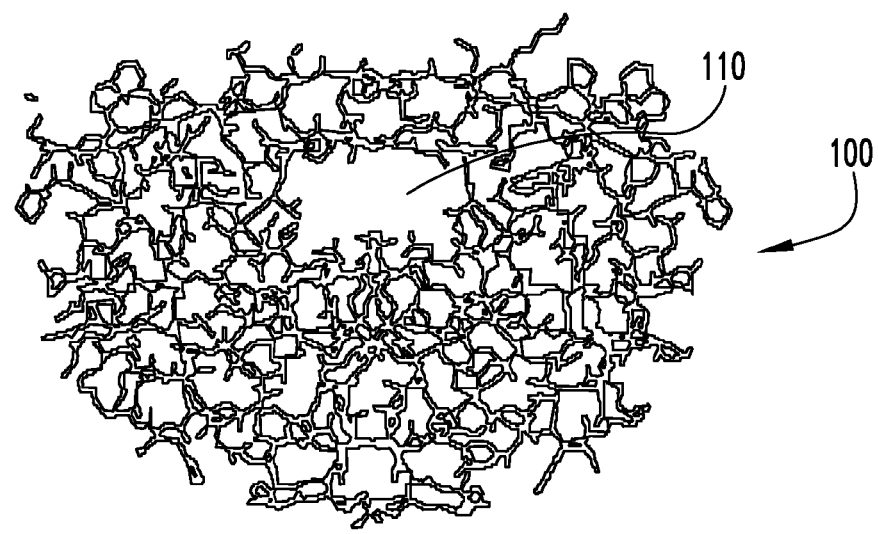
FIG. 1 is an example of an active site.
Figure 2:
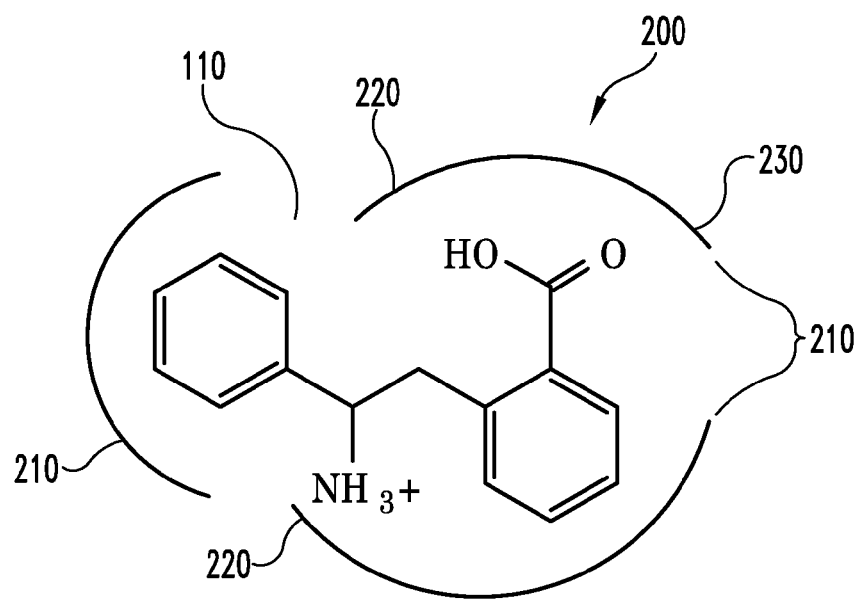
FIG. 2 is a schematic illustration of typical ligand-receptor binding interactions.
Figure 3:
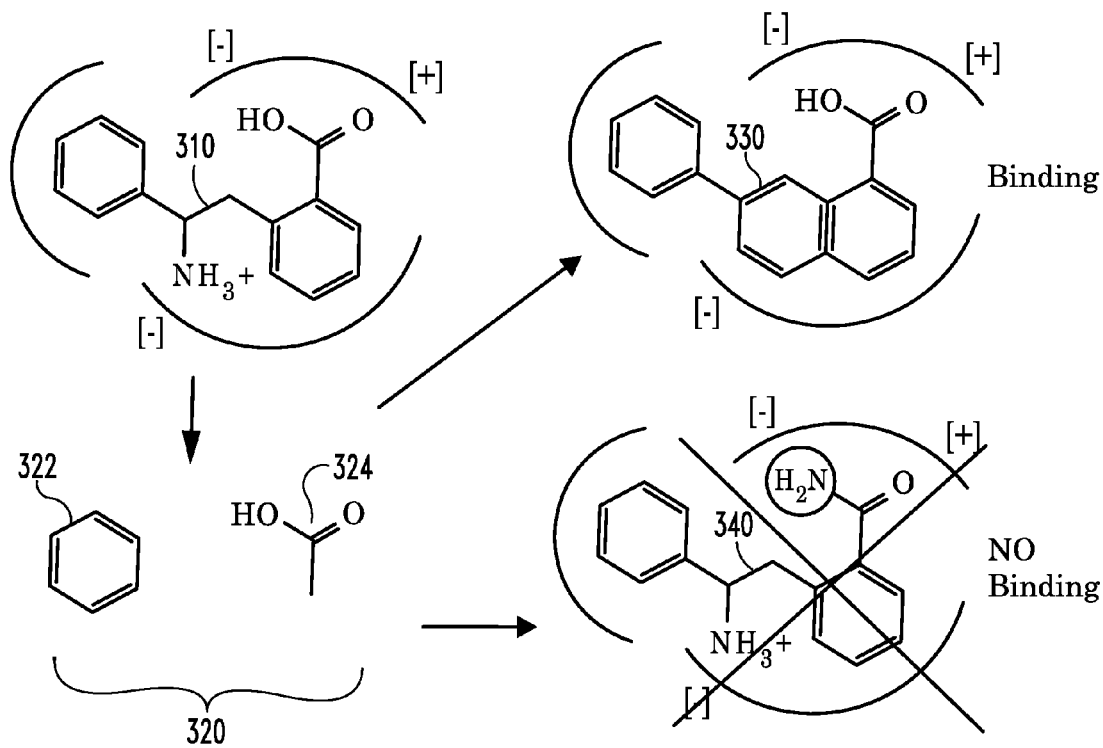
FIG. 3 is a schematic illustration of a pharmacophore and its relationship to ligand-receptor binding.
Figure 4A:
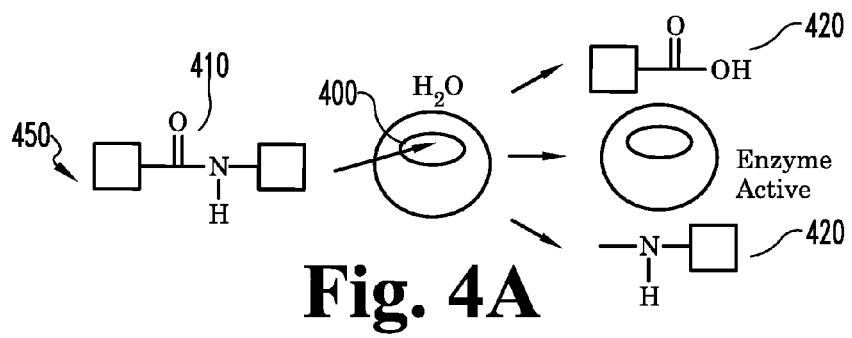
FIGS. 4A and 4B schematically illustrate the biochemical mechanism of a protease, and its inactivation through ligand manipulation.
Figure 4B:
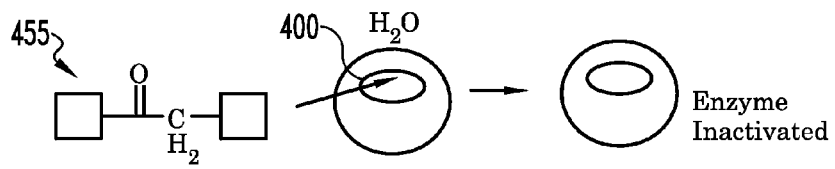
Figure 5:
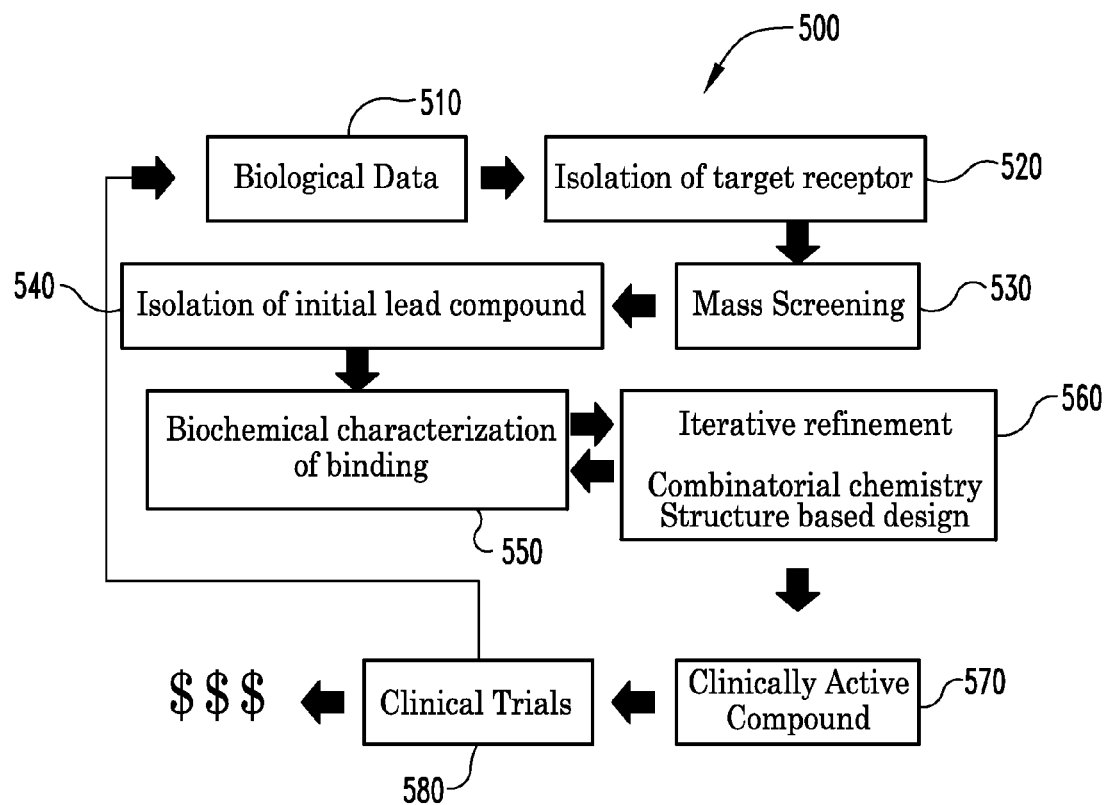
FIG. 5 is a diagram of a typical drug design pipeline, in which a system and method according to the present invention may advantageously be used.
Figure 6A:
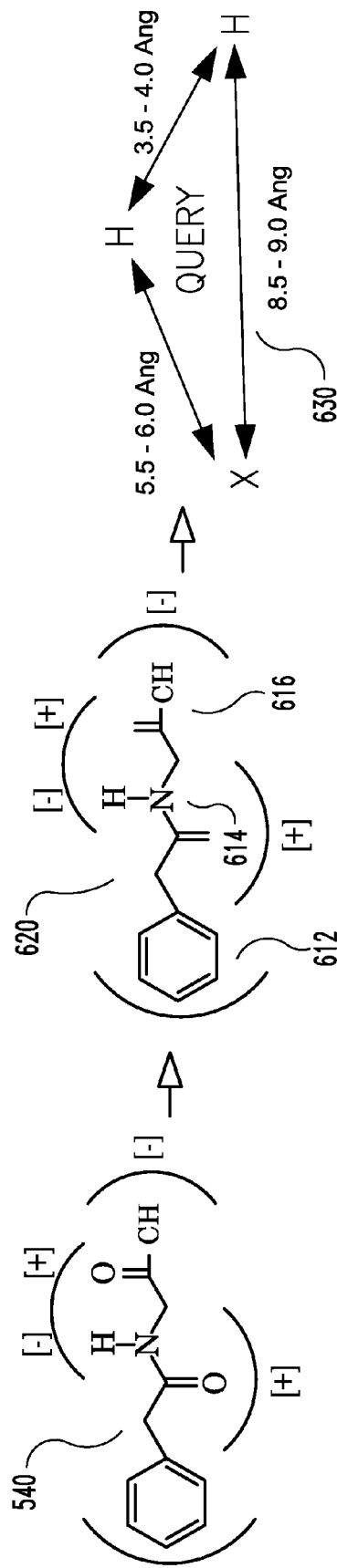
FIGS. 6A and 6B schematically illustrate how scanner-type prior art drug design programs operate.
Figure 6B:
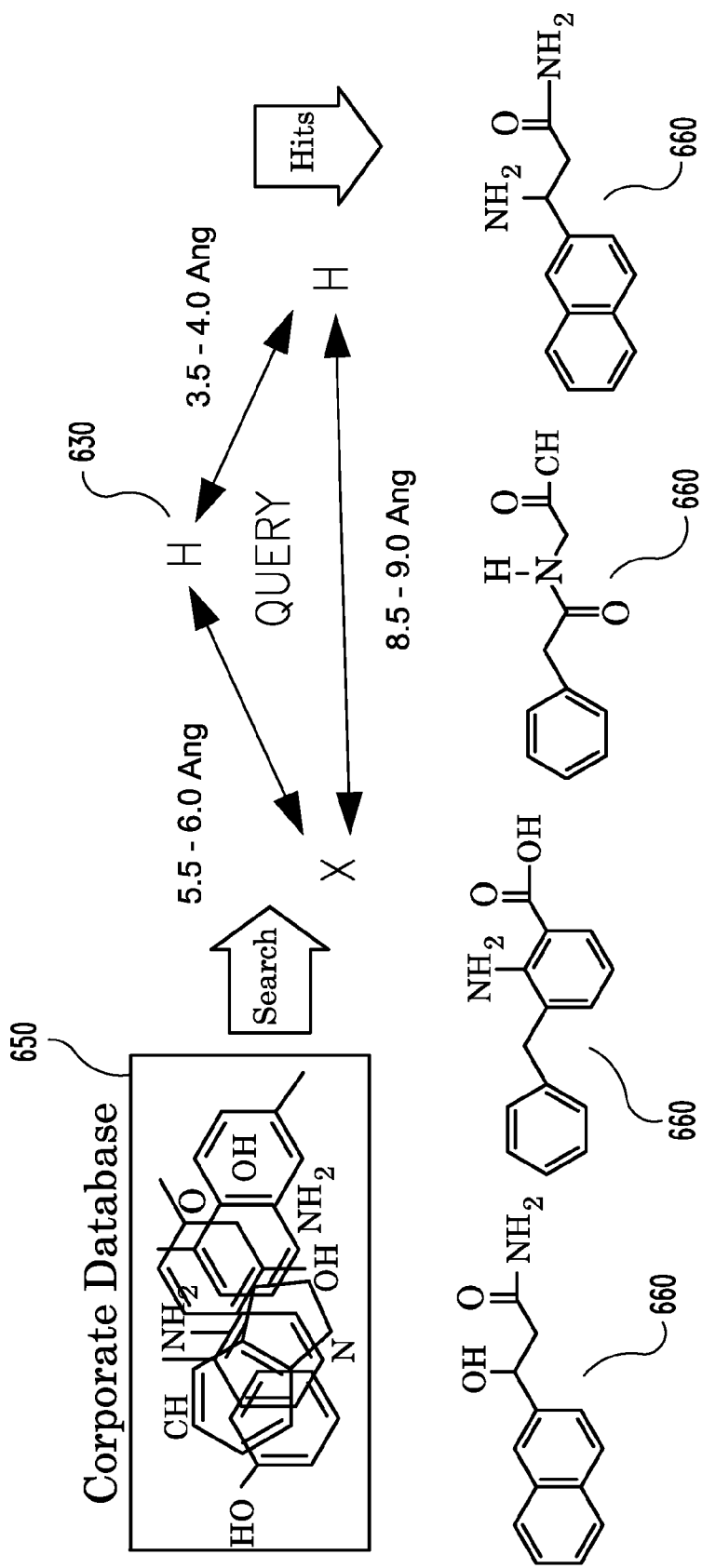
Figure 7:
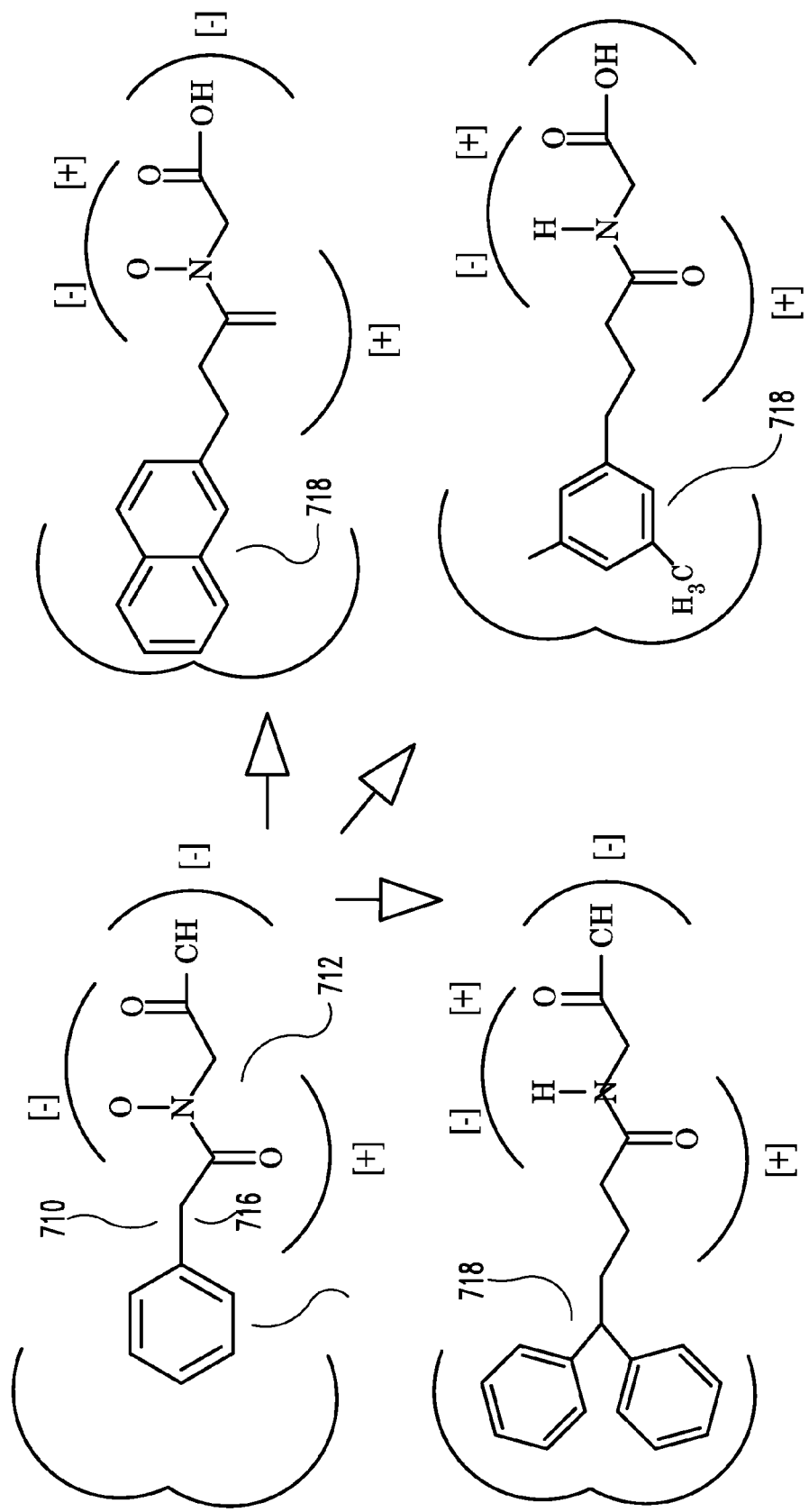
FIG. 7 schematically illustrates how builder-type prior art drug design programs operate.
Figure 8:
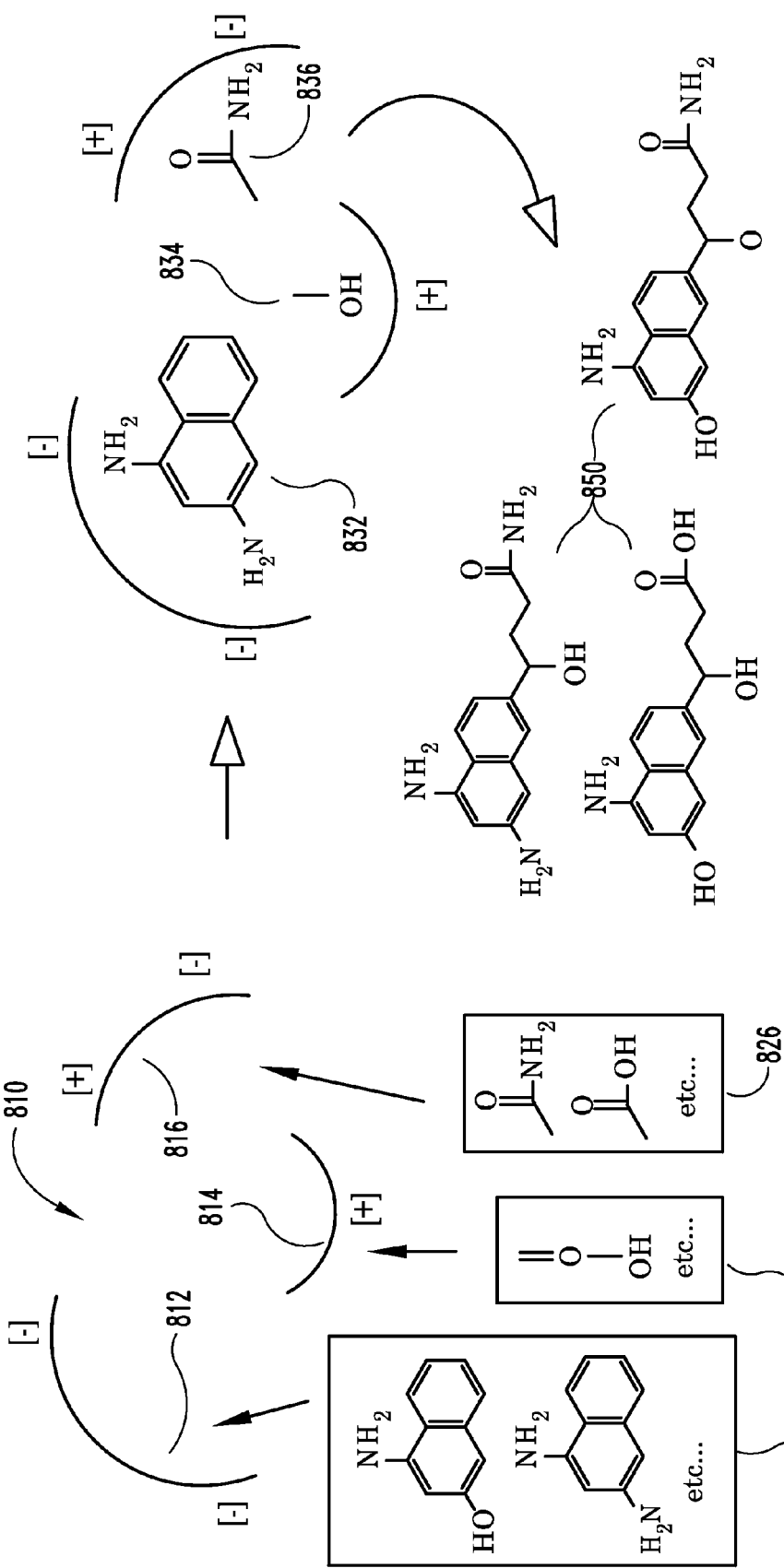
FIG. 8 schematically illustrates how hybrid-type prior art drug design programs operate.

For the purposes of promoting an understanding of the principles of the invention, reference will now be made to the embodiment illustrated in the drawings and specific language will be used to describe the same. It will nevertheless be understood that no limitation of the scope of the invention is thereby intended. Alterations and modifications in the illustrated device, and further applications of the principles of the invention as illustrated therein are herein contemplated as would normally occur to one skilled in the art to which the invention relates.

A preferred embodiment improved system for computer-aided drug design according to the present invention provides greatly improved efficiency of computational methods, to much more rapidly and efficiently generate new drugs. The present invention provides rapid minimization techniques to improve the efficiency of conformational searching. Using the present invention enables the virtual screening of entire corporate databases and massive combinatorial libraries in hours, instead of weeks. The present invention allows computational chemists to more intelligently design virtual libraries to explore the development of novel pharmaceuticals. This makes it possible to refine potential drug candidates against flexible protein targets and multiple active site presentations. This is a capability that pharmaceutical companies have sought for some time.

For the purposes of this document, the terms "chemical structure" and "structure" refer to any collection of atoms that are chemically bonded. The terms "group" and "rigid group" refers to any structure that lacks any rotatable bond. For example, an amide bond (—CONH—) is both a structure and a rigid group, but a sugar molecule is a structure and not a group. Those skilled in the art will appreciate that, technically, water contains two rotatable bonds: two O—H bonds. Thus, water is a structure that contains rotatable bonds by chemical definition. However, rotating the O—H bond does not alter the structure of the water molecule since the hydrogen just rotates in place about the bond axis. Consequently, for the purposes of this document, the O—H bonds in water are not treated as rotatable bonds, and $H_2O$ is both a structure and a group. Likewise, other hydrogen single-bonds are treated as non-rotatable, since they also do not give rise to different shapes when the bond rotates.

A preferred embodiment improved method for computer-aided drug design comprises generating a component database by pulling building block components from a user's structure database; generating diversity indices for the component groups that describe one or more chemical properties of the groups; selecting a lead compound for optimization; and creating generations of derivative compounds by replacing substituent fragments of compounds from one generation with component groups from the component database to create subsequent generations of compounds. During the creation of derivative compounds, the replacement of fragments is performed randomly during earlier generations, but is performed by a combination of a heuristic active site mapping algorithm and an intelligent component selection method in later generations. Referring to FIG. 15, a flowchart is shown for a preferred embodiment computer program that implements the above-described method, as described in greater detail hereinbelow.

FIGS. 9A and 9B schematically illustrate the process of generating a component database 910 by pulling rigid components from a user's database 901, such as a corporate database. Note that the typical corporate database 901 will contain hundreds of thousands of structures 905. Chemical structures are composed of rigid, non-rotatable chemical groups 915 separated by rotatable bonds, as defined by the laws of chemistry and known to those skilled in the art. These rigid groups 915 are isolated by identifying the rotatable bonds 920 in the structures 905. The individual rigid groups 915 are then tagged with a component label and stored in the component database 910 along with their three-dimensional atomic coordinates and descriptions of their chemical composition. The component label is used to register each fragment and prevent the storage of redundant chemical groups. The descriptors of each group record chemical information characterizing the associated group, including the size of the component, atom composition, connectivity, hydrogen bond donor and acceptor groups, ring structure, and electrostatic charge.

Using the stored chemical attributes, all components 915 in the component database 910 are sorted and mapped into a multi-dimensional array called the "diversity index". In this array, each axis represents a different chemical property. In one embodiment, only size, polarity, and valence are mapped. Preferably, other group traits are described and included in the component database 910 diversity index as well. Each axis of the array provides a gradient along which components 915 can be distinguished. Components 915 that are similar with respect to the various descriptors are grouped together along that axis. By generating this diversity index, a measure of the chemical diversity in the component database 910 is provided. More importantly, a means of rapidly cross-referencing and retrieving chemical components 915 in the database with respect to desired chemical properties is provided.

It will be appreciated that the component database 910 will typically be much smaller than the structure database 901 from which it is generated. For example, a typical corporate database 901 might contain approximately 100,000 structures 905 that consist of different combinations of only 5,000 rigid groups 915, so that the component database 910 would be only 5% of the size of the user's structure database 901. Nevertheless, depending on the size and diversity of the user's structure database 901, the component database 910 may be any size.

Once the component database 910 has been generated lead compounds can be selected and optimized. Regions of the lead compound that degrade receptor-binding affinity are replaced by groups from the component database 910 to generate new compounds. In an iterative fashion, these regions of the new compounds are then replaced to create further generations of new compounds. In the preferred embodiment, the selection of components 915 from the component database 910 is random during the early generations of substitutions in order to help ensure adequate sampling of the database and to help generate novel solutions.

In later generations, however, the preferred embodiment employs a heuristic active site mapping algorithm to determine superior chemical characteristics to complement a given region of the active site. Over time, the preferred embodiment maintains a record of chemical components 915 that improve ligand-receptor interaction along with their three-dimensional location within the active site. The heuristic active site mapping algorithm employs this data to generate a corresponding three-dimensional map that details the optimal chemical features, such as electrostatic charge and volume, that a group must possess to bind within a specific region of the active site, as illustrated in FIG. 10. The active site of the receptor 1001 in FIG. 10 is more positively charged at the ends, with respect to the indicated axis 1010, and more negatively charged in the middle. The active site 1001 is generally oblong, and narrower at one end. These features correspond to the graphs of charge 1020 and size 1030.

In the preferred embodiment, during later generations of derivation an intelligent component selection system is used to select optimal derivative components. The intelligent component selection system uses a heuristic active site mapping algorithm to learn, over time, the three dimensional location and chemical characteristics of the optimal components that bind the active site. This information is then applied to screen the component database 910, using the diversity index described above, to isolate chemical components 915 that are similar to the features specified by the active site map to create lists of candidate fragments. These fragments are then used to derivatize the lead compound in a combinatorial fashion to generate ligands with improved receptor complementarity.

Figure 11:
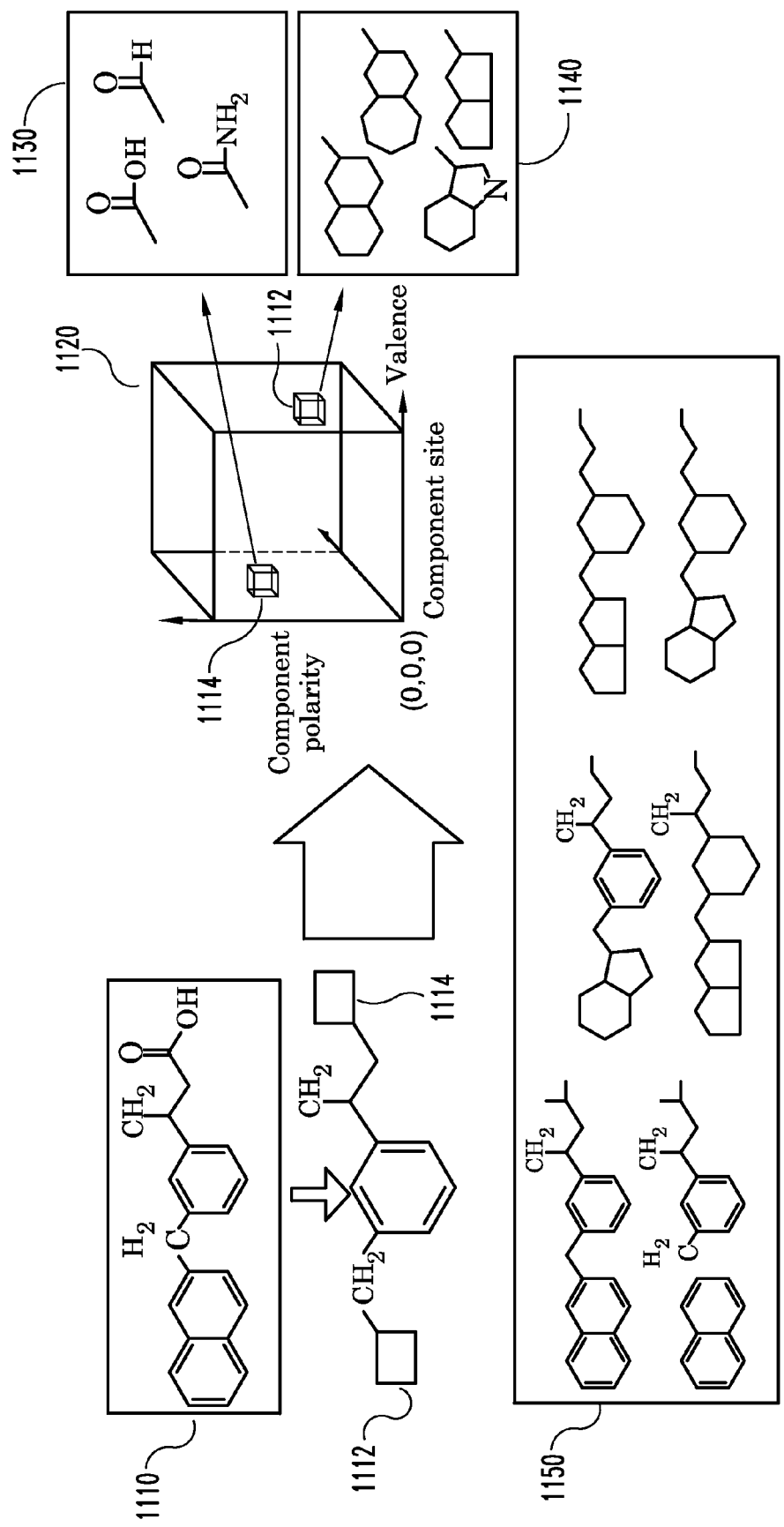
FIG. 11 schematically illustrates the creation of derivative compounds using a heuristic active site mapping algorithm according to the present invention that employs only component size, valence, and polarity.

FIG. 11 schematically illustrates an example of the later-generation creation of a derivative compound using an intelligent component selection system according to the present invention. In the example shown, the intelligent component selection system uses a heuristic active site mapping algorithm according to the present invention employing only component size, valence, and polarity. In this example, the naphthalene group 1112 and carboxylic acid group 1114 of a ligand derivative 1110 have been selected for replacement with other component groups. As the diversity index graph 1120 shows, the naphthalene group 1112 is large and very non-polar, since it is a bi-cyclic ring structure and is strictly hydrocarbon. Conversely, the carboxylic acid group 1114 is quite small, but highly polar. Assume that, using an active site map as described above, it is determined that these characteristics are ideal for complementing the receptor at each respective component. The diversity index is used to cross-reference and extract other components 915 from the component database 910 that exhibit similar characteristics, such as those shown in the set of small, polar groups 1130 and in the set of large, non-polar groups 1140. These components 915 are then combinatorially used to generate a new family of derivatives, such as those shown in the group of derivatives 1150. Each derivative retains the good receptor binding characteristics, but enough variability is generated to potentially improve receptor complementarity.

In the preferred embodiment, a component specification language is also used to give the computational chemist the ability to help select component groups for substitution that are most likely to improve the binding affinity of a derivative compound. The component specification language contains a combination of keywords, target values, and Boolean operators. A brief summary of sample commands appropriate for the component specification language is listed below:

| Command | Function |
| --- | --- |
| CMPNTS min-max | Number of total components to utilize. |
| ATOMS min-max | Number of atoms in a specific component. |
| R-ATOMS min-max | Number of ring atoms in a specific component. |
| MW min-max | Molecular weight. |
| LINKS atypes (<,>,=) value | Specifies rotatable bond atom types between components. |
| ATYPES (list) (<,>,=) value | Specifies atom type requirements in a specific component. |
| BONDS (list) (<,>,=) value | Specifies bonded atom types within a specific component. |
| PHARM (atype) {x,y,z} | Specifies a specific pharmacophoric group at coordinates {xyz}. |

Once the chemical requirements are established for each derivative group the master component database 910 is filtered using the component specification language to generate individual databases used to select groups for substitution for each subsite.

Figure 12:
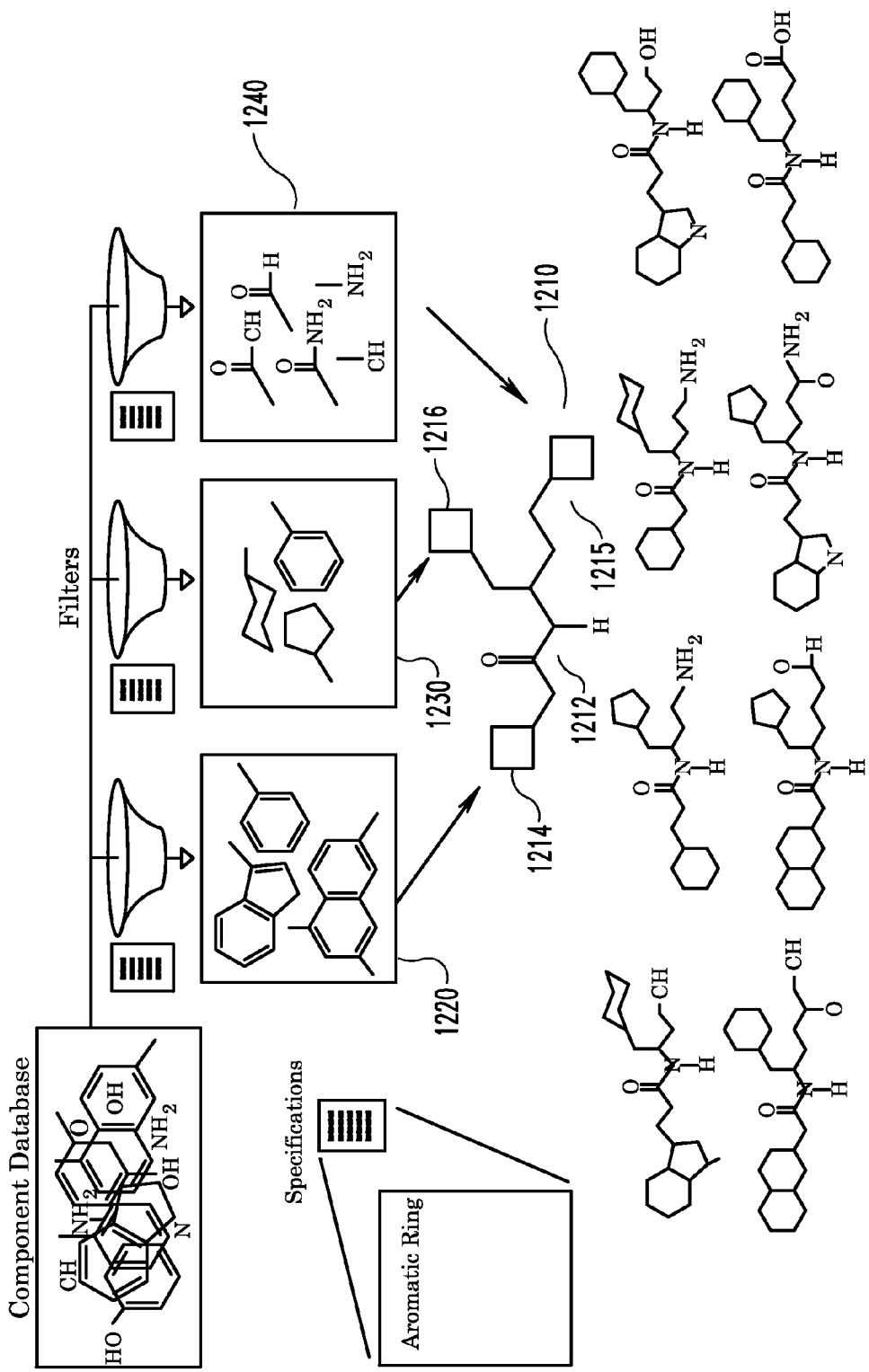
FIG. 12 schematically illustrates an example of user-directed structure generation according to the present invention for a sample lead compound.

FIG. 12 illustrates an example of the use of the component specification language to generate new lead compound derivatives. The lead compound 1210 comprises a scaffold containing an amide bond 1212 with a first side chain 1214, a second side chain 1216, and a third side chain 1218 extending from it. In this example, assume that a biochemical characterization of this lead compound reveals that three chemical groups make up the pharmacophore. The first group 1220 must contain a large ring system. Crystallographic analysis reveals that both single and bi-cyclic rings are capable of binding, as long as they are planar. Thus, they must be aromatic. Any atom types may be accepted. The second group 1230 again requires a cyclic component, but the binding pocket in this region is smaller and more spherical. Thus, only single rings are acceptable, and they need not be aromatic. In addition, this region is very hydrophobic; thus, only hydrocarbon components 915 are acceptable (only carbon and hydrogen). The third group 1240 fits a region of the active site that is highly charged, and so requires a small polar group. Thus, no ring structures are acceptable and heteroatoms are required. With these chemical requirements established the computational chemist can employ the component specification language to filter the master component database 910 to generate individual sub-databases. In other words, the groups 1220, 1230, and 1240 are populated by filtering the master component database 910 to select only those components 915 which match the criteria selected and implemented through the component specification language. All possible derivatives within the constraints of the active site can then be combinatorially generated.

In the preferred embodiment the component specification language also permits the removal of undesired structures. For example, in the preferred embodiment, the ATOM and RATOM constraints described above govern how many atoms a particular component can possess. The LINK constraint likewise limits the atom types that can be used in the rotatable bonds. The PHARM specification signifies that a specific atom type must be present at a precise location in the active site. The #CMPNTS restriction places upper and lower bounds on the total number of components 915 a structure can possess. The ATYPE constraint stipulates how many atoms of a specific type can be present in both individual components 915 as well as the entire structure. The BOND specification places limits on the bonded atom types that can be present within a component. Collectively, these commands provide the user with great flexibility in defining undesirable structures and elements of structures. The component specification language permits these definitions to be used as an integral part of the generation of derivative compounds, in order to channel computer resources into the generation of potentially viable structures.

In the preferred embodiment, the component specification language also permits the user to define chemical templates to direct the generation of derivative compounds. A template comprises a set of specific user-defined components 915, each of which comprises one or more chemical criteria as specified by the component specification language, separated by wildcard designations, which denote where chemical variability can occur. So, for example, the user might define a template containing a carbonyl group separated from a phenyl group by one wildcard, and separated from a particular hydrocarbon chain by a second wildcard. Template-driven structure generation will then produce chemically diverse structures in which various appropriate components 915 replace the wildcards, while the hydrocarbon chain, carbonyl group, and phenyl group remain constant. In the preferred embodiment, constraints can also be placed on the wildcard regions in order to control the range of variation, so as to, for example, preserve the spatial location of the constant components 915 with one another.

Figure 13:
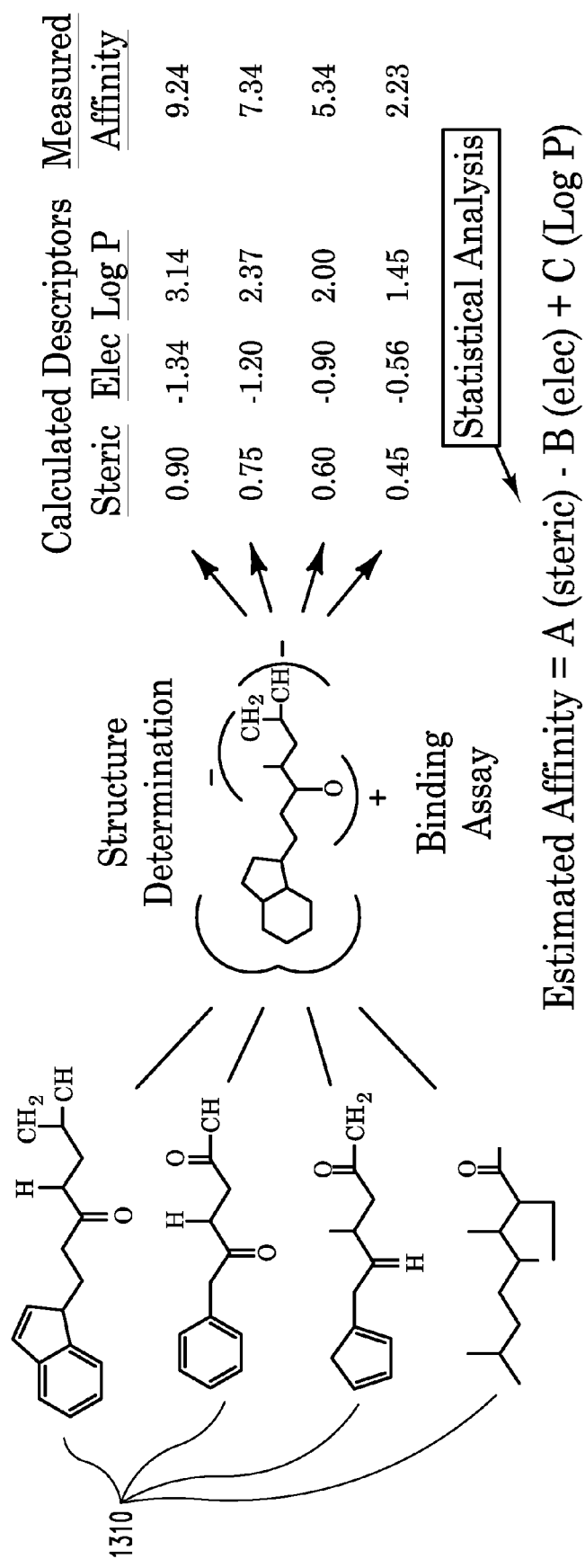
FIG. 13 schematically illustrates an example of a calculated scoring function derived from four complexes whose binding affinity has been measured and whose descriptors have been calculated.

In the preferred embodiment, focused scoring functions are used to calculate the receptor binding affinity for the newly generated derivative ligands. As will be known to those skilled in the art, scoring functions estimate ligand-binding affinity using descriptors that can be measured from the ligand receptor interaction. In essence, a scoring function is an equation that relates measurable descriptors of binding to ligand receptor affinity. FIG. 13 illustrates an example derivation of a scoring function using four complexes 1310 whose binding affinities have been measured and whose descriptors have been calculated. Statistical tools, such as partial least squares regression, are employed to generate the equation relating the numerical trends in the various descriptors, including steric complementarity, electrostatic energy, and hydrophobicity, with the corresponding binding affinities. The resulting equation is the scoring function, which provides an estimated affinity as a function of the calculated descriptors. Note that the example shown in FIG. 13 is quite simplistic—a typical scoring function may contain 20 or more terms. Nevertheless, scoring functions only very crudely estimate the Gibbs free energy of the reaction.

Compounding this problem is the fact that most prior art commercial packages use a single generalized scoring function that has been derived using a wide variety of structures. There are two significant problems with this approach. Firstly, receptor systems vary considerably in their chemical makeup. In some systems, electrostatic interactions dominate the ligand binding force. In other systems, hydrophobic interactions overshadow the other forces involved. Using a variety of ligand receptor systems in the training set can add considerable noise to the data, which diminishes its predictive power. Secondly, when the generalized scoring function is integral to the software package, this again injects developer bias into the solutions that will be generated.

The preferred embodiment incorporates statistical and analytical tools that allow the user to generate focused scoring functions to estimate ligand binding to a specific target receptor using structure-activity data the user may have specific to the target receptor being studied. This allows, for example, companies who have characterized the receptor binding of a number of lead compound derivatives to utilize this knowledge in the derivation of the focused scoring functions. By limiting the training set to structures binding within the same receptor, we bias the scoring function towards the interactions that govern ligand association with the target active site. Thus, if hydrophobic contacts predominate, the hydrophobic descriptors will be emphasized. If electrostatic forces are important to binding, those descriptors will be accentuated. Even something as simple as the size of the active site can have a tremendous impact on the allowable ligands. This is a descriptor that would be lost given a multitude of different training set receptors. As such, focused scoring functions have far more predictive power with respect to estimating ligand-receptor binding than generalized scoring functions.

Even with structure-activity data pertaining to a target receptor, difficulties in generating accurate scoring functions may arise, as depicted in FIGS. 14A, 14B, and 14C. Firstly, there must be an adequate number of compounds to make the analysis statistically valid. In each graph, the dots schematically represent the structure-activity data of a collection of ligands bound to a target receptor. The lines passing through them represent potential scoring functions attempting to describe their distribution. The graph in FIG. 14A illustrates an ideal distribution of complexes that allows for an easy determination of a best-fit line. This data set contains a large number of complexes whose activity covers a wide range of values. A scoring function generated from this set thoroughly represents the data. The graph in FIG. 14B is a more representative of the situation most often faced in academic research. Here there are too few compounds to generate an accurate fit of the data. Notice the ambiguity that exists in determining the best-fit curve. Any scoring function derived from this dataset has little predictive value. The graph in FIG. 14C is another scenario that might occur. Here, there is no lack of data. However, given money and time constraints in drug development projects, it can be difficult to justify crystallographic studies on poorly binding compounds. As such, crystal structures of compounds are usually determined only when high affinity structures have been found by assay. Therefore, a cluster of high-affinity data points is produced. As one can see from FIG. 14C, it is also difficult to elucidate an accurate scoring function when the structure activity data is not broad enough.

In the preferred embodiment, when it is determined that the derived scoring function offers little predictive value, a focused target function is then used. A target function is formed by simply averaging the descriptor values of the highest affinity training set complexes. This produces a target point in multidimensional descriptor space, where each dimension is a measured chemical descriptor. In effect, the target function is a scoring function that is derived from a single point, rather than a best-fit line. Compounds are scored using an inverse-distance function from the target point. Those derivative structures whose descriptor values are closest to the target have higher scores and are retained, while those further from the target are scored lower and are rejected.

It will be appreciated that the target function is easy to implement. A large training set of compounds is not required. Even a single compound can be used as a model for optimal ligand receptor binding. By simply extracting the descriptor values of the best compounds, many of the pitfalls in scoring function development that result from data artifacts are avoided. In addition, the characteristics of the ligand-receptor association that foster improved binding are allowed to drive the development of future structures. Conversely, the principle disadvantage of using target functions is the lack of extrapolation. In other words, target functions constrain the system using the properties of previously characterized ligands. Thus, target functions are not well suited to predict whether a new derivative compound can bind better to the receptor than our best compounds. Target functions are also not well suited to quantitate the binding relative to the other structures in the training set. While the system is employing target functions, it is simply building structures that mimic the characteristics of the best compounds. However, this is often precisely the task at hand for pharmaceutical chemists. By the time a drug development project has reached maturity, the ligands that have been developed are often optimal binding compounds. Therefore, a target function is usually sufficient as it allows the drug designer to construct alternative chemical architecture that retains optimal binding characteristics.

In order to use the preferred embodiment system according to the present invention, the user must first input parameters for the design task. These parameters preferably include: the crystal structure of a lead compound that is to be optimized; the regions of the lead compound that are to be replaced and optimized; and the user's database of known compounds, including proprietary compounds. The input parameters may also advantageously include structure-activity data of previously characterized compounds.

Once the input parameters are provided, the user first uses the system to specify the regions of the lead compound that must be replaced to improve receptor binding. A lead compound normally contains a region of high receptor complementarity (the scaffold) attached to regions that diminish binding. These regions are referred to as optimization sites. Each optimization site is separated from the scaffold by an "anchor bond", which provides the attachment point for the addition of replacement components 915. The user simply selects the anchor bonds to designate the regions that will be optimized by the preferred embodiment system.

The user then uses the system to create a component database 910 from the user's structural database by extracting and registering chemical building-block fragments. With each component registered in the database, the system stores the 3D atomic coordinates along with numerous other chemical properties—including size, atom types, bond types (connectivity), and electrostatic charge. The user also uses the system's component specification language to establish restrictions governing generation of derivative compounds. The user may also advantageously use the system to generate focused scoring functions, target functions, or both, using structure-activity data from previously characterized compounds.

The user can then use the system to generate the derivative compounds. The user must specify the number ("N") of derivative structures to be generated and retained in each iteration, and the number of iterations that the system must complete without finding a new compound before the system will terminate the operation. The system then iteratively substitutes new groups for portions of the lead compound that were identified for optimization.

In each iteration, the system generates N/2 different derivatives by random selection of components 915 from the component database 910. Components 915 are added to the anchor bond, and connectivity information that was extracted from the original user's database is used to assemble the fragments. Components 915 are chemically joined according to the laws of chemistry and within the user-defined constraints as specified by the component specification language.

In each iteration, the other N/2 derivatives are generated by intelligent component selection. A previously generated derivative is selected at random, and a random number of its components 915 are selected for replacement. For each component to be replaced the chemical characteristics most likely to complement the receptor at that location are determined using the heuristic active site map. These characteristics are then used to select a list of suitable replacement fragments by cross-referencing the diversity index of the component database 910. From this list, a new component is selected at random.

At the end of each iteration, the system has a total of 2N derivative structures; N from the previous iteration, and N from present one. Component specifications are then used to remove combinations of structures that have been identified by the input parameters to be unacceptable (because they cannot be economically synthesized, because they are toxic, etc.). The system then performs a conformational search for each surviving compound to identify the conformation with the highest binding affinity (which can be determined by either a scoring function or a target function, depending on the input parameters and the present iteration). This conformation is retained and the others are discarded. The compounds are ordered based on their binding affinities, and the top N compounds are retained for the next iteration. The process continues until no additional unique compounds are retained for the number of iterations that was selected by the user.

Figure 15B:
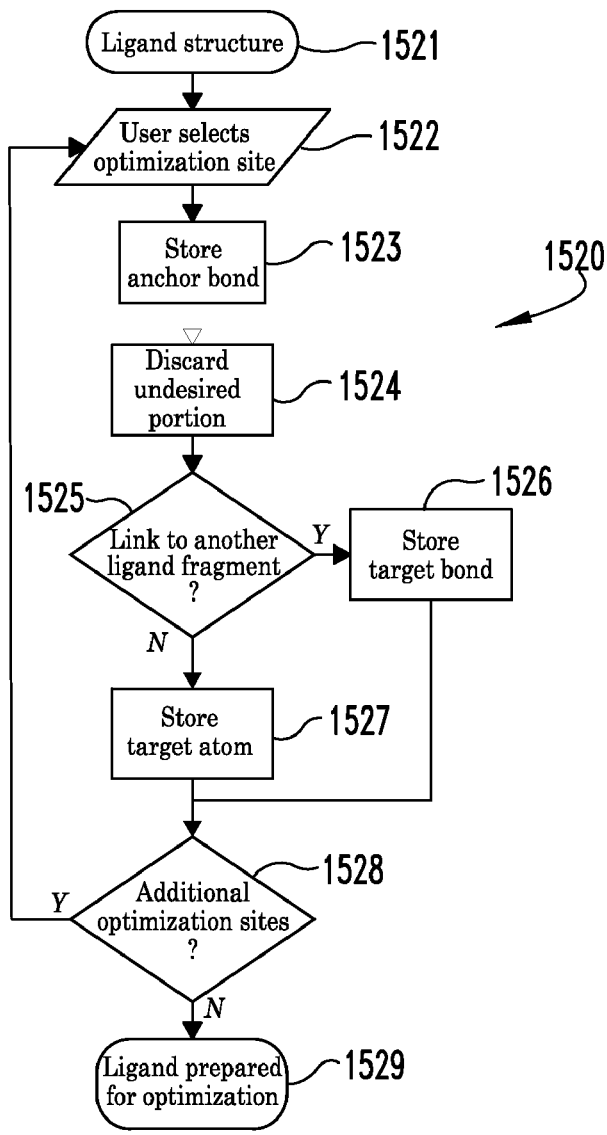
Figure 15C:
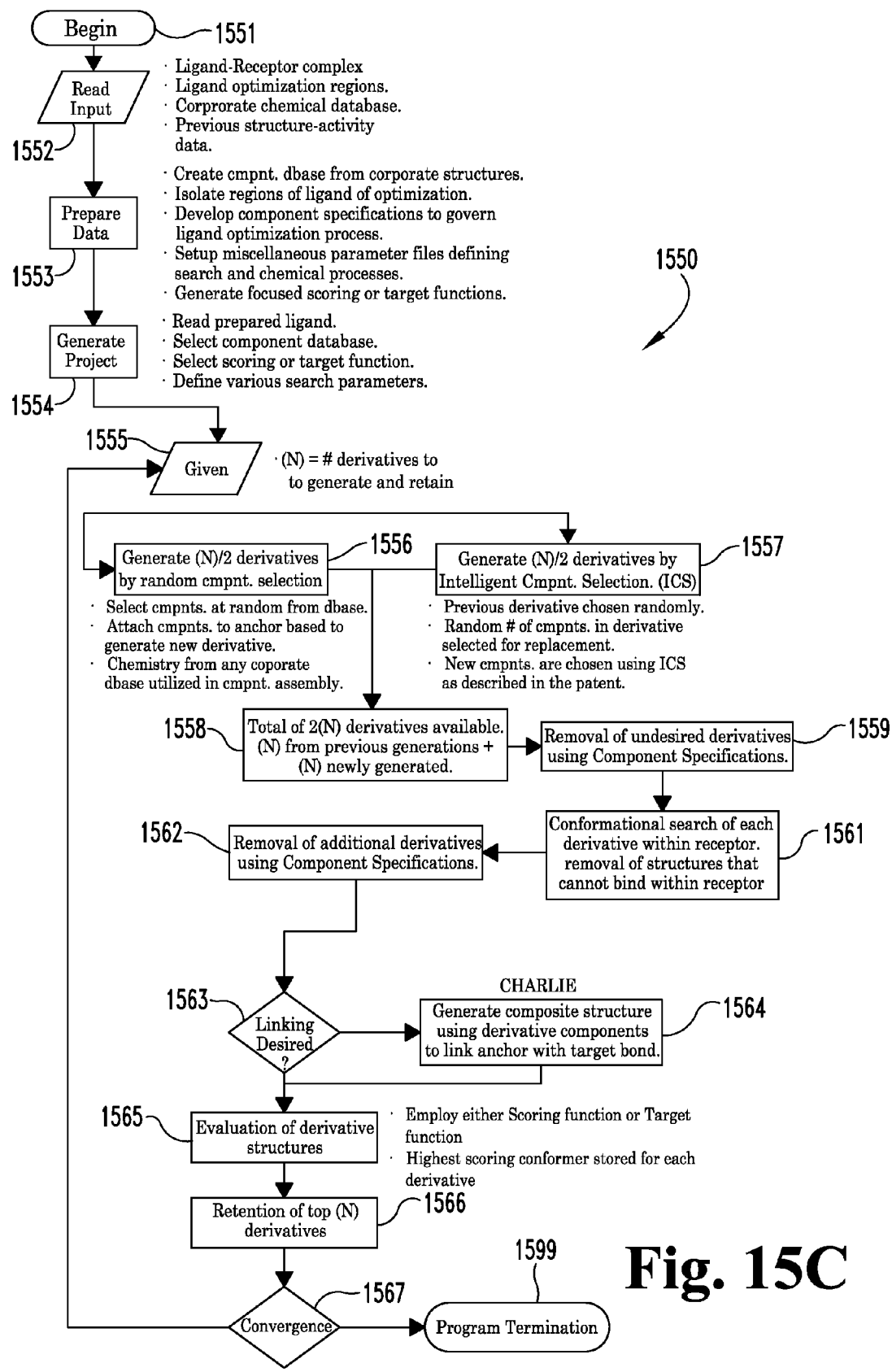
Figure 16A:
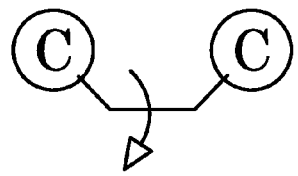
FIGS. 16A and 16B illustrate the use of minimization to improve sampling efficiency.
Figure 16B:
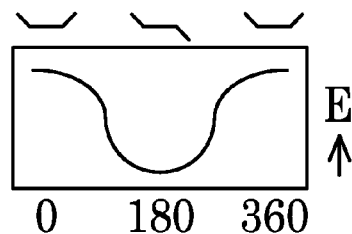

FIGS. 15A, 15B, and 15C show flowcharts for a computer program that implements the above-described method. The program includes a component database preparation subroutine 1510, as shown in FIG. 15A, a ligand preparation subroutine 1520, as shown in FIG. 15B, a scoring function preparation subroutine 1540, as shown in FIG. 15A, and a ligand optimization subroutine 1550, as shown in FIG. 15C.

The ligand optimization subroutine 1550 begins at 1551. At 1552 the process input is read, including the atomic coordinates of the ligand-receptor complex (the natural ligand and receptor, "docked" together), the ligand optimization regions as determined in subroutine 1520 below, the user's database 901 (assuming one is being used), and whatever structure-activity data is available. At step 1553 the data is prepared. The component database 910 is constructed from the user's database 901, and regions of the ligand are isolated for optimization by the subroutines 1510 and 1520, respectively, as described in greater detail hereinbelow. Component specifications are developed to govern the ligand optimization process, and appropriate parameter files are set up defining the search and the chemical processes (including, for example, the number of structures (N) to retain after each iteration). Scoring or target functions, or both, are prepared, as appropriate, by the subroutine 1540, as described in greater detail hereinbelow. At 1554 the ligand optimization project is generated. The prepared ligand is read, the desired component database is selected, and the appropriate scoring or target function is selected. Any limitations on component specification or search parameters are chosen.

At 1555 the number "N" of derivatives to be generated in each generation is selected. At 1556 half of the selected number of derivatives is generated by random component selection. Each of these derivatives is created by selecting components at random from the component database 910 to attach at each of the identified anchor bonds. Although selected randomly from the database 910, the selection of components may be restricted by various search parameters and component specifications set out at step 1554. At 1557 half of the selected number of derivatives is generated by intelligent component selection. Each of these derivatives is generated by selecting one of the previously generated ligands (either at 1556, or in a previous generation of derivation), and selecting a random number of component substructures in the previously generated ligand for replacement. Those component substructures are then replaced with components that are expected to provide higher receptor-binding activity as dictated by a heuristic active site mapping algorithm, as discussed in greater detail hereinabove with respect to FIG. 11.

At step 1558 there are 2N derivatives available, N from the previous generation and N from the present generation. At step 1559 species that are undesirable regardless of conformation are removed using the component specifications set out at step 1554, so that computer resources are not devoted to useless conformational searching. Then at 1561 a conformational search of each remaining derivative is performed to find the best-binding conformation for each remaining compound. At step 1562 additional undesired derivatives are removed using the component specifications set out at step 1554. At step 1563 it is determined whether linking is desired. If so, at step 1564 composite structures are generated by connecting the anchor bond with the target bond via derivative components. After step 1564, or 1563 if linking is not being performed, at 1565 the 2N derivative structures are evaluated according to the scoring or target function. At step 1566 the lower-scoring N derivative structures are removed. At step 1567 the surviving N structures are compared to the surviving N structures from the previous generation to determine whether the process has converged (i.e., whether there are at least a pre-determined number of new derivatives in the present generation that were absent from the previous generation). If the process has not converged, the program returns to steps 1556 and 1557 to create a new generation of derivatives. Otherwise, the program terminates at 1599.

The subroutine 1510 for constructing a component database 910 from a user's database 901 begins at 1511. At 1512 the first unread structure in the user's database 901 is read. At 1513 the rotatable bonds of the read structure are identified, and used to partition the structure into component groups. At 1514 it is determined whether any of these groups are absent from the component database 910. If so, the new group or groups are stored in the component database 910, in association with an appropriate tag identifying the group and its features, including geometry, etc., as described hereinabove. After the new groups are stored, or if no new groups were identified, it is determined whether all structures have been read from the user's database 901. If not, the subroutine 1510 returns to step 1512, otherwise, the subroutine 1510 terminates at step 1517.

The subroutine 1520 for preparing a ligand for optimization begins at 1521. At 1522 the user selects a site on the ligand for optimization. At 1523 the atoms defining the anchor bond separating the region to be optimized from the scaffold are stored. At 1524 the portion of the ligand distal to the anchor bond is removed from the ligand's structure. As described above, in the preferred embodiment components from the database are combinatorially added to the anchor bond in order to optimize ligand-receptor interactions. In addition, in the preferred embodiment the user can link one ligand scaffold to another in order to generate composite ligands by bridging the space between. At 1525, if the user wishes to bridge to another ligand scaffold a target bond is selected at 1526 and stored. This bond will serve as a target towards which the developing derivative chain will be grown and attempt to splice. If linking is not desired, a target receptor atom is instead selected at 1527 and stored. This target receptor atom directs the growing derivative chain to ensure that the appropriate region of the active site will be filled and optimized. At 1528 it is determined whether the user wishes to optimize any additional sites on the ligand. If so, the subroutines 1520 returns to 1522, otherwise the subroutine terminates at 1529.

The subroutine 1540 for preparing scoring or target functions begins at 1541. At 1542 receptor binding data is input. At 1543 a predictive scoring function is generated using partial least squares regression ("PLS"), as described earlier. At 1544 it is determined whether the scoring function model generated at 1543 is predictive. If not, a target function is selected at step 1545. After step 1545, or 1544 if the scoring function was determined to be predictive at 1544, at 1546 the user can perform modifications of the coefficients and scalars of the scoring or target function. At 1549 the subroutine ends.

Figure 17:
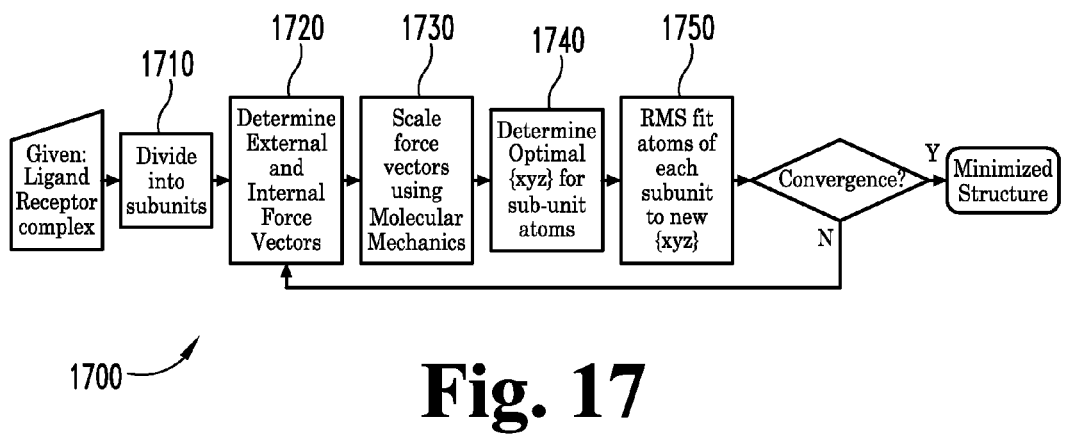
FIG. 17 is a flowchart diagramming a preferred embodiment of a method according to the present invention.

FIG. 17 is a flow chart illustrating a preferred embodiment improved method 1700 according to the present invention. The method 1700 iteratively nudges non-deformable ligand subunits to minimize external and internal forces. Each subunit is a collection of atoms whose coordinates remain fixed with respect to one another. At 1710, the subunits are generated by dividing the ligand at each rotatable bond, as discussed hereinabove. Thus, each subunit is preferably a group. Nevertheless, it will be appreciated that the method 1700 can be performed with subunits that include rotatable bonds, though doing so will generally degrade the performance of the method 1700.

The subunits essentially act and move independently to minimize high-energy contacts while optimizing favorable energetic interactions with the receptor. The rotatable bonds give the subunits the flexibility to rotate and maneuver. However, they ensure that the structural integrity of the ligand is not compromised. Preferably, ring systems are considered en-bloc subunits, though it will be appreciated that many ring systems include theoretically rotatable bonds.

Figure 18A:
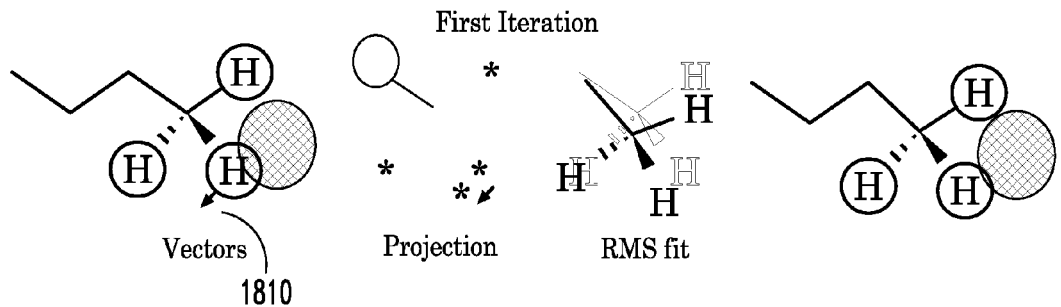
FIGS. 18A and 18B illustrate internal and external force vectors used to iteratively displace subunits in the preferred embodiment shown in FIG. 17.

Each subunit is processed in turn, as follows. First, all external force vectors are determined. External force vectors are the result of perturbations to one or more subunit atoms from non-bonded interactions, both attractive and repulsive, with the receptor. Each force vector designates the direction and magnitude a subunit atom must be displaced to optimize receptor interaction. Since the subunit must move en-bloc to minimize the external forces, it exerts internal forces upon neighboring units via the rotatable bonds, potentially altering their position and geometry. FIG. 18A illustrates this first iteration processing, with an example external force shown as 1810.

Figure 18B:
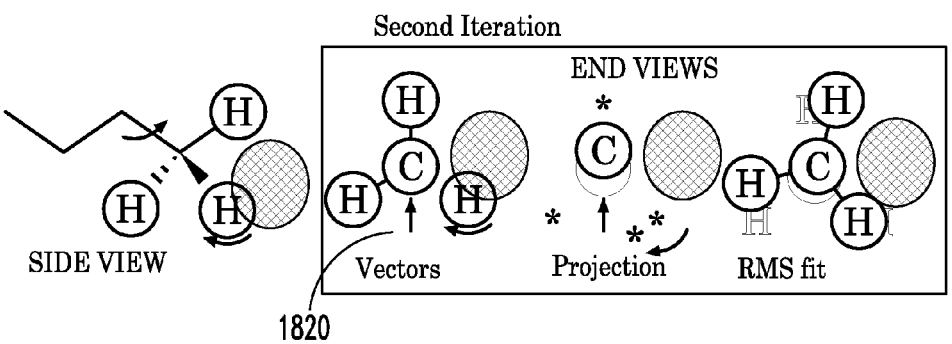

The neighboring subunits push back in successive iterations and exert stabilizing internal forces, shown as 1820 in FIG. 18B, upon the atoms of the displaced subunit. Once all external and internal force vectors have been calculated, they are scaled by their molecular mechanics contributions. Steric violations generate the highest energy; thus, displacements that resolve them take precedence. Geometries that either stretch or compress bond lengths are next in priority. Bond angle distortions are then considered. Finally, alterations in torsion angles are of much less importance. As such, the process consistently implements atom displacements that result in the greatest reduction of energy. This is a critical aspect of the process, as it ensures that the optimal minimization path is taken along the energy surface as rapidly as possible.

Figure 19:
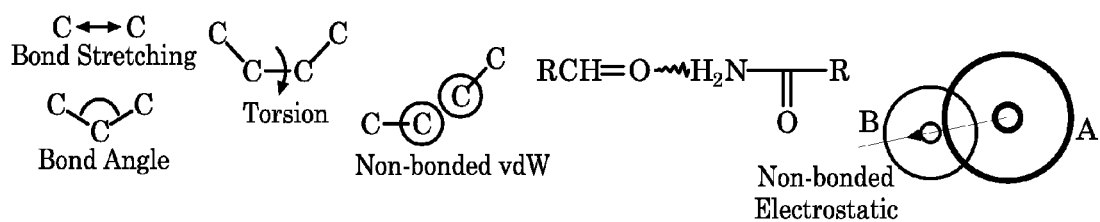
FIG. 19 is a schematic illustration of the molecular mechanics parameters preferably used in the method shown in FIG. 17.

New coordinates are generated for each member atom of the subunit by projecting the scaled external and internal force vectors acting upon that atom. Some subunit coordinates will usually be significantly displaced. Usually, others will be untouched. The new position of the ligand segment is then determined by performing an RMS fit of the subunit coordinates onto the new coordinates with restrictions regarding minimum and maximum displacement. In so doing, the subunit is usually displaced to a slightly more optimal position. This in turn, influences neighboring subunits. All other subunits are processed in this manner. Through multiple iterations, not only are torsion angles altered, but segments also gradually translate and rotate in concert to optimize receptor interaction energy. These cycles proceed until convergence occurs. Convergence is defined when successive iterations produce structures whose coordinates differ by less than a user-defined distance threshold. FIG. 19 illustrates an example in which a high-energy steric contact can be relieved in two iterations by a low-energy change in the torsion angle while bond angles remain constant.

In the presently preferred embodiment, step 1710, the division of ligand and receptor into subunits is performed as follows. Starting at any ligand atom as a seed, a breadth-first search is implemented to "grow" collections of atoms belonging to individual subunits. Preferably, the Tripos Mol2 file format is implemented as input. (Tripos, Inc. 1699 South Hanley Rd., St. Louis, Mo. 63144; www.tripos.com). This file format contains a listing of all rotatable bonds and their associated atoms. As such, the breadth-first search traverses the ligand, grouping subunit atoms with one another until a rotatable bond is processed. The rotatable bond demarcates the next subunit and grouping proceeds accordingly until the entire ligand has been processed.

In the presently preferred embodiment, step 1720, the determination of external and internal force vectors, is performed as follows. It will be appreciated that force vectors result any time an atom pair violates a molecular mechanics parameter. FIG. 20 illustrates each of the molecular mechanics parameters used in the presently preferred embodiment. The molecular mechanics parameters of the Tripos Force Field is preferably used because it offers the widest coverage of potential ligand pair atom types. (Tripos, Inc. 1699 South Hanley Rd., St. Louis, Mo. 63144; www.tripos.com). It will be appreciated, however, that fewer than all of these parameters may be used, though generally this will degrade performance. It will also be appreciated that alternative sets of parameters could be used to describe the same mechanisms; the particular parametric math employed is immaterial to the present invention.

The force vector on a given atom, B, as a result of another atom, A, has an origin (x,y,z) at the coordinates of the atom B. The ideal position for atom B to minimize the force field violation, B', is then calculated, holding the position of atom A constant. The force vector is then B→B'. The vectors for each of the component atoms in the subunit are totaled to generate a total force vector, which determines the direction in which the subunit is displaced. Thus, the direction of displacement of the subunits is actually a real-space direction.

In the presently preferred embodiment, step 1730, the scaling of force vectors using molecular mechanics parameters, is performed as follows. As previously stated, preferably the effects of minimization are replicated using force vectors to calculate the atomic positions for optimal structure relaxation. A critical aspect of the method is the relative scaling of the force vectors with respect to molecular mechanics parameters. The scaling of the force vectors determines the relative contributions of each parameter to the overall energy as a function of deviation from norm. Thus, these scaling factors determine the Cartesian coordinate projection that will offer the greatest reduction in energy per iteration of minimization. Optimization of these factors is therefore an important driver of the quality of the minimization paths that are taken along the energy surface. The scaling factors determine how well the relaxation algorithm will replicate well-established minimization protocols.

In the presently preferred embodiment, a Monte Carlo approach to optimization of the scaling factors is used. For example, a number of well-characterized ligand-receptor complexes from the PDB may be minimized, using well-established force fields. In each case, the ligand can be slightly perturbed with respect to the receptor, and allow it to relax. Using these structures as pre- and post-minimization controls, an automated batch procedure can be used to vary the scaling factors, to relax the pre-minimized structures, and then to determine the RMS deviation between relaxed and minimized-control complexes. Preferably, this procedure is run iteratively, and the scaling factors that generate results most similar to full-blown minimization are retained. Although the Tripos Force Field is preferably used, it will be appreciated that any suitable force field may be used.

In the presently preferred embodiment, step 1740, the determination of optimal coordinates for units and RMS fitting, 1750, are performed as follows. The scaled force vectors, as stated above, determine the (x,y,z) coordinate projection that will offer the greatest reduction in energy per iteration of minimization. Thus, optimal coordinates for each ligand sub-unit atom are calculated by summing all the scaled force vectors on that atom. The RMS fit of the optimal coordinates loci are preferably determined using the BMFIT algorithm, (Nyburg, S. C., Acta Cryst. B30, (1974) 251-253), because it performs geometric fitting with minimal calculation, and because it is easily implemented. However it will be appreciated that any suitable algorithm may be used.

A number of procedures can be used to optimize the execution of a method according to the present invention. The BMFIT procedure uses a number of transformations to perform the necessary operations for fitting. These can be optimized using appropriate matrix operations. Lookup tables can be implemented for trigonometric functions and square root operations. In addition, hash functions previously implemented in software packages marketed by Tripos can be used to further expedite the calculation of non-bonded interaction energies.

Preferably, a method according to the present invention includes steps for imposing user-defined constraints on minimization, including receptor flexibility and pharmacophore data. As previously discussed, it is valuable that biochemical and biophysical receptor data be brought to bear on the ligand-receptor optimization process. Doing so greatly improves the likelihood that an optimized ligand is actually a practical drug. In the presently preferred embodiment, the user can specify regions of receptor flexibility. It has been found that users normally allow a region of the receptor within a desired distance of the ligand to relax during minimization. If more rigidity is required, the user can also limit this region to the receptor side chains while the backbone remains fixed. In the presently preferred embodiment, these are implemented as default methods, and do not require any user-input.

It will be appreciated that for certain receptor targets a wealth of crystallographic data are available. Pharmaceutical companies, in particular, have the resources to fully characterize a system in this manner. The receptor is co-crystallized with numerous ligands, each possessing unique chemistry, shape, and charge distribution. As such, the effect of the various ligands on the resulting active site structure allow one to deduce and tally the relative motions of each receptor residue. If only a single structure is available, temperature factor and occupancy data may be helpful. Since the methods according to the present invention iteratively calculates the optimal coordinates for the various ligand and receptor atoms, these measurements can be employed to tether the residue displacement from the starting structure. In addition RMSD measurement from NMR experiments can be used. It will be appreciated that this process can be fully automated.

Alternatively, statistical data gleaned from the Protein Databank can be used. Average sidechain mobility and the propensity for certain protein folds to wiggle can be exploited. Preferably, the user can simply "highlight" specific areas of the receptor to relax by selecting the endpoints of the regions. A depth-first search will be employed to capture all the pertinent residues.

Pharmacophore data is also valuable to the ligand discovery process. In certain existing software, functionality has been provided that automatically elucidates regions of potential ligand interaction within the receptor active site. (Ho, C. M. W., and Marshall, G. R., Cavity Search: An Algorithm for the Isolation and Display of Cavity-like Binding Regions, Journal of Computer-Aided Molecular Design, (1990) 4:337-354.) This functionality is advantageously included in software according to the present invention. In conjunction with user-supplied data, this permits the rapid rejection of ligands that fail to meet pharmacophoric requirements, as well as guiding the minimization process.

For example, functional group requirements can eliminate deficient ligand candidates prior to searching. Distance constraints between key pharmacophoric elements can be used as a discriminant to reject ligand conformers prior to minimization. These distances can also act as constraints during the minimization process to ensure that reasonable receptor bound conformers are generated. Occupancy and vacancy requirements for user-defined regions of 3D space can be implemented by monitoring ligand-receptor atom coordinates during minimization. This can also provide another mechanism for rejection of conformers prior to minimization. Also, critical hydrogen bonding requirements can be used as another discriminant for non-compliant ligands. Otherwise, favorable ligand-receptor electrostatic interactions provide external force vectors that guide the ligand into more plausible binding modes.

It will be appreciated that the concept of concerted receptor motion is a feature of considerable interest in structure-based design. Upon binding, certain receptors undergo very specific, yet potentially large structural changes that can be characterized or confirmed through NMR or crystallographic analysis. In some cases, this trajectory could include a branch point, which defines which of two or more states a receptor will adopt in response to ligand binding. Using vector projection methods the relaxation of specific receptor regions can be constrained to a precise trajectory. This enables the user to design ligands to interact with a clearly defined moving receptor target. This information can be presented to the program in any of a number of suitable ways. Multiple receptor snapshots may be read that detail the range of motion upon binding. The trajectories can them be calculated, and the paths stored for use in constraining the minimization.

It will be appreciated that most current docking software positions ligands within a static receptor. Although the ligand is allowed to flex, the complex is not routinely minimized prior to scoring because of the computing time requirements. As described above, rapid minimization methods according to the present invention increase the efficiency of finding accurate low-energy states while diminishing the computational burden associated with conformational searching. The resulting speed-ups in both minimization and in conformational searching allow the use of docking functionality that considers both ligand and receptor flexibility, thereby enabling the rapid, accurate determination of optimal ligand-receptor poses.

Preferably, conformational searching is performed on the ligand in question, and several of the best poses, in terms of receptor interaction energy, are stored using a scoring function, as described above. In the presently preferred embodiment, scoring functions from software commercially available from Tripos (RACHEL) are used. Poses are preferably evaluated on the fly using clustering methods to ensure they are from different regions of conformation space, lest they all minimize to the same well. Minimization is then performed to relax these structures to more accurately determine their bound conformation. The number of poses processed in this manner can be adjusted to adjust minimization speed.

The heuristics discussed above with respect to pharmacophore data can also be used to implement receptor flexibility, for identifying mobile regions of receptors. The conformational search can be performed on the ligand within the active site using van der Waals radii that have been reduced. Typically, vdW radii are scaled 90-95% of normal in order to accommodate conformations that would be missed due to relaxation of bond angles. However, in order to allow for receptor flexibility, even smaller vdW radii can be implemented during the conformational search. This permits ligand atoms to approach receptor atoms much more closely. Again, the top poses are stored, calculating the energetics of the system using reduced atom size. However, as minimization is implemented, the vdW radii are rescaled back to normal. As such, the enlarged vdW radii allow the ligand to displace the receptor residues as needed, provided that biophysical data supported the range of motion.

While the invention has been illustrated and described in detail in the drawings and foregoing description, the same is to be considered as illustrative and not restrictive in character. Only the preferred embodiment, and certain alternative embodiments deemed useful for further illuminating the preferred embodiment, has been shown and described. All changes and modifications that come within the spirit of the invention are desired to be protected.

I claim:

1. A method for computer-aided molecule design, the method comprising:

executing an adaptive sampling function and rapid minimization function, the rapid minimization function employing iterative fitting of multi-atomic subunits of a molecule, the multi-atomic subunits including subunits having a plurality of non-hydrogen atoms, the multi-atomic subunits being fitted by perturbing the location of the multi-atomic subunits, while keeping the coordinates of the constituent atoms of a given subunit fixed with respect to all of the other constituent atoms of that subunit, in a real-space direction that reduces potential energy;

wherein the rapid minimization function perturbs the real-space position of the multi-atomic subunits by calculating a scaled force vector for the subunits' constituent atoms, and then solving for new coordinates for the constituent atoms using root mean square fitting onto the new coordinates, while still keeping the coordinates of the constituent atoms of each subunit fixed with respect to one another, the scaled force vectors resulting from non-bonded interactions with a receptor and from bonded interactions with neighboring subunits, and the scaled force vectors being scaled according to molecular mechanics contributions to resolve steric violations first, geometries that stretch or compress bond lengths second, bond angle distortions third, and alterations in torsion angles last; and wherein the adaptive sampling function and rapid minimization function are executed on a computer.

2. The method of claim 1 further comprising determining the optimal six-dimensional coordinates for units using RMS fitting.

3. The method of claim 1 wherein force vectors are also determined for electrostatic sources of potential energy.

4. The method of claim 1, wherein the multi-atomic subunits include only non-rotatable bonds.

5. The method of claim 2, wherein the multi-atomic subunits are bonded to each other only by rotatable bonds.

6. The method of claim 1, further comprising performing an iterative conformational searching function having minimization function as an element of conformational searching iterations.

* * * * *